United States Patent [19]
Turner et al.

[11] Patent Number: 5,344,435
[45] Date of Patent: Sep. 6, 1994

[54] URETHRAL INSERTED APPLICATOR PROSTATE HYPERTHERMIA

[75] Inventors: Paul F. Turner; Theron N. Schaefermeyer, both of North Salt Lake; Amer M. Tumeh, Salt Lake City; Philip A. Terry, Salt Lake County, all of Utah

[73] Assignee: BSD Medical Corporation, Salt Lake City, Utah

[21] Appl. No.: 609,372

[22] Filed: Nov. 5, 1990

Related U.S. Application Data

[63] Continuation-in-part of Ser. No. 225,307, Jul. 28, 1988, Pat. No. 4,967,765.

[51] Int. Cl.$^5$ ............................................. A61N 5/02
[52] U.S. Cl. .................................. 607/101; 607/102; 607/113; 607/156; 128/736
[58] Field of Search ............................ 128/784–786, 128/804, 736, 401; 607/101, 102, 97, 105, 154, 156, 113, 116

[56] References Cited

U.S. PATENT DOCUMENTS

| | | | |
|---|---|---|---|
| 2,936,761 | 5/1960 | Snyder | 128/349 |
| 4,046,139 | 9/1977 | Horn | 128/2 H |
| 4,154,246 | 5/1979 | LeVeen | 128/784 |
| 4,311,154 | 1/1982 | Sterzer et al. | 128/804 |
| 4,312,364 | 1/1982 | Convert et al. | 128/804 |
| 4,448,198 | 5/1984 | Turner | 128/422 |

(List continued on next page.)

FOREIGN PATENT DOCUMENTS

| | | | |
|---|---|---|---|
| 105677A | 9/1983 | European Pat. Off. | |
| 0370890 | 5/1990 | European Pat. Off. | 128/804 |
| 1512622 | 10/1989 | U.S.S.R. | 128/784 |
| 8103616 | 12/1981 | World Int. Prop. O. | 128/804 |

OTHER PUBLICATIONS

Andrew Wu, et al., "Performance Characteristics of a Helical Microwave Interstitial Antenna for Local Hyperthermia", Mar./Apr. '87, Med. Phys, 14(2), pp. 235–237.

(List continued on next page.)

Primary Examiner—Lee S. Cohen
Attorney, Agent, or Firm—Mallinckrodt & Mallinckrodt

[57] ABSTRACT

A method for the treatment of the prostate gland which heats the tissues which would otherwise be surgically removed with a trans-urethral resection of the prostate. This method is accomplished by combining a radiating energy device integrated with a urinary drainage Foley type catheter, which is modified to provide cooling along the urethra surfaces. The radiating device also serves as a means to measure the tissue radiated thermal energy for the control or monitoring of temperature of the prostate tissues being heated. A urethral inserted applicator for prostate hyperthermia includes a multi-tube, balloon type catheter. The catheter includes a fluid dry tube for an energy radiator antenna applicator which also serves as a radiometric temperature sensor for measuring the temperature of the prostate tissue, and an open fluid receiving tube. An electromagnetic energy generator supplies electromagnetic energy to the applicator. A comparator is connected to the temperature output of the radiometer, and a temperature reference potentiometer for comparing the actual tissue temperature level with a desired temperature level and outputting control signals to the electromagnetic generator for controlling the output to the applicator. The microwave operated applicator is preferably an elongated coil having the tip end connected to the center conductor of a coaxial cable and the opposite end connected to the outer conductor of the coaxial cable. A sheet or sheath of insulation material covers the microwave coil antenna for insulating the coil from the tissue and the thickness of the sheet may be varied to provide uniform tissue heating along the length of the coil. The ultrasound operated applicator is preferably one or more ultrasound crystal cylinders to radiate energy into the tissue and convert tissue thermal ultrasonic energy into electrical energy for measurement by a radiometer. The balloon of the catheter engages the body's bladder to position the applicator properly during the treatment.

20 Claims, 14 Drawing Sheets

U.S. PATENT DOCUMENTS

| | | | |
|---|---|---|---|
| 4,469,103 | 9/1984 | Barrett | 128/401 X |
| 4,524,550 | 7/1985 | Ruggera et al. | 128/1.5 |
| 4,583,556 | 4/1986 | Hines et al. | 128/804 |
| 4,601,296 | 7/1986 | Yerushalmi | 128/804 |
| 4,658,836 | 4/1987 | Turner | 128/804 |
| 4,662,383 | 5/1987 | Sugawa et al. | 128/784 |
| 4,669,475 | 6/1987 | Turner | 128/399 |
| 4,676,258 | 6/1987 | Inokuchi et al. | 128/804 |
| 4,681,122 | 7/1987 | Winters et al. | 128/736 |
| 4,700,716 | 10/1987 | Kasevich et al. | 128/804 |
| 4,712,559 | 12/1987 | Turner | 128/422 |
| 4,798,215 | 1/1989 | Turner | 128/804 |
| 4,813,429 | 3/1989 | Eshel et al. | 128/736 |
| 4,860,752 | 8/1989 | Turner | 128/422 |
| 5,007,437 | 4/1991 | Sterzer | 128/786 |

OTHER PUBLICATIONS

El-Deek M. El-Sayed et al., "Use of Sheath Helix Slow-Wave Structure as an Applicator in Microwave Heating Systems" 1981, Journal of Microwave Power, 16 (3&4), pp. 283-288.

Jozef Mendecki et al., "Microwave Applicators for Localized Hyperthermia Treatment of Cancer of the Prostate", Nov. '80, Int. J. Radiation Biol. Phys., vol. 6, No. 11, pp. 1583-1588.

Tadashi Harada, et al., "Microwave Surgical Treatment of Diseases of Prostate", Urology, Dec. '85 vol. XXVI No. 6, pp. 572-576.

Ding-Jiu Li, et al. "Design & Thermometry of an Intracavitary Microwave Applicator Suitable for Treatment of Some Vaginal & Rectal Cancers", Nov. '84 Int. J. RadiationOncology Biol. Phys. vol. 10, pp. 2155-2162.

Leonid Leybovich, et al., "Intracavitary Hyperthermia: A newly Designed Applicator for Tracheal Tumors"- Jan. '87, Endocurietherapy/Hyperthermia Oncology, vol. 3, pp. 23-29.

Toru Satoh, et al., "Thermal Distribution Studies of Helical Coil Microwave Antennas for Interstitial Hyperthermia", Int. J. Radiation Oncology Biol. Phys. vol. 15, pp. 1209-1218.

P. B. Dunscombe et al., "Heat Production in Microwave-Irradiated Thermocouples", Med. Phys. 13 (4), Jul./Aug. 1986.

R. T. Constable et al., "Perturbation of the Temperature Distribution in Microwave Irradiated Tissue Due to the Presence of Metallic Thermometers", Med. Phys. 14 (3), May/Jun. 1987.

Leonard S. Taylor, "Electromagnetic Syringe" IEEE Transactions on Biomedical Eng., vol. BME-25, No. 3, May 1978.

Medical Tribune, vol. 29, No. 9, Thursday, Mar. 31, 1988, "Transurethral Hyperthermia for BPH: Trial's Goal is to Top 80% Success", by Rick McClure, pp. 3, 13, 14.

M. A. Astrahan, et al., "Microwave Applicator for Transurethral Hyperthermia of Benign Prostate Hyperplasia" May/Jun. 1989, International Journal of Hyperthermia, vol. 5, No. 3, pp. 283-296.

Chris J. Diederich et al., "Induction of Hyperthermia Using an Intracavitary Multielement Ultrasonic Applicator" IEEE Transactions on Biomedical Engineering, vol. 36, No. 4, Apr., 1989.

A. Lindner et al., "Local Hyperthermia of the Prostate Gland for the Treatment of Bening Prostatic Hypertrophy and Urinary Retention" British Journal of Urology, 1987, 60, pp. 567-571.

A. Yerushalmi, et al., "Localized Deep Microwave Hyperthermia in the Treatment of Poor Operative Risk Patients with Benign Prostatic Hyperplasia" May 1985, vol. 133, pp. 873-876.

URETHRAL INSERTED APPLICATOR PROSTATE HYPERTHERMIA

RELATED APPLICATIONS

This application is a continuation-in-part of copending application Ser. No. 07-225,307 filed Jul. 28, 1988, now U.S. Pat. No. 4,967,765.

BACKGROUND OF THE INVENTION

1. Field

This invention relates to energy radiation devices for medical hyperthermic purposes, and more particularly to a combined catheter, and energy applicator for treating prostatomegaly such as benign prostatic hypertrophy, prostatitis, and prostate malignancy by urethral insertion.

2. State of the Art

Hyperthermia or induced high body temperature has been considered beneficial in treating various human diseases including many types of cancer. More specifically, various types of malignant growths are considered by many researchers to have a relatively narrow hyperthermia treatment temperature range. Below a threshold temperature of about 41.5 degrees Celsius, thermal destruction of these malignancies is not possible, and in fact their growth may be stimulated. However, at temperatures above a range of about 43 to 45 degrees Celsius thermal damage to most normal body tissue cells occurs if exposure lasts for even a relatively short duration.

Many types of superficial cancers are known to respond to direct application of surface heat. Deeply located malignant growths are most difficult to heat to the desired temperature without damaging overlying healthy tissue, owing to limited penetration depth of externally applied energy, tissue blood flow, and heat transfer properties of the body. A solution to this problem has been the development of electromagnetic (EM) or ultrasound (US) radiation heating devices for inducing hyperthermia. This form of treatment is historically known as "diathermia". The EM frequency range preferred is that of the microwave range which is generally defined as that above 300 MHz, although the lower defined microwave band extends to 225 MHz.

EM or US radiation heating of subsurface growths from an exterior surface is ordinarily enabled by configuration and placement of one or more applicators and by appropriate selection of EM or US radiation frequency, phase and intensity. Nevertheless, tissue growths inside of, or in close proximity to, heat sensitive tissue or organs, are much more effectively and safely heated by EM or US radiation irradiating applicators positioned within the body as closely as possible to the growth requiring treatment.

The advantages of positioning EM or US radiation applicators relatively close to the growth to be heated by radiation include improved heating control, more localized heating, less possibility of overheating adjacent healthy tissue, and more direct treatment of the enlarged tissues causing the undesirable symptoms.

Close applicator access to certain types of diseased tissue growth is provided by surgical procedures for naturally occurring body passages such as the esophagus, larynx, prostate gland and colon. Surgical procedures enlarge the passage by cutting away the diseased tissue. Some heating methods involve placing small EM radiation applicators over the tissue or in an incision to provide direct irradiation of the growth. An illustrative type of a body passage insertable EM radiation applicator is described in U.S. Pat. No. 2,407,690 issued to Southworth. The Southworth type body passage EM applicators have been configured to cause a heating pattern that tends to be concentrated at the radiating tip of the applicator and which decreases at a usually exponential rate from the radiating or distal tip towards the proximal end of the applicator toward the power supply.

Special and difficult problems often attend growths found along natural body passages. For example, diseased tissue tends to spread around and along the passage, often in a relatively thin layer. Typically, the patient problems are confined to originate from a tissue layer which is less than one centimeter thick, and may extend as far as 6–10 centimeters along the passage. The use of Southworth type applicators result in nonuniform irradiation heating of the elongated growth. Thus, the temperature at the distal tip of a Southworth type applicator may have to be so hot that it kills surrounding healthy tissue in order to make the proximal end hot enough to kill the unwanted tissues in that zone.

Rectally inserted rigid and non-flexible antenna devices have been designed for heating of the prostate. Examples of such devices are disclosed in U.S. Pat. No. 4,601,296 issued to Yerushalmi, and a 1980 article titled "Microwave Applicators for Localized Hyperthermia Treatment of Cancer of the Prostate," by Mendecki et al., Int. J. Radiation Oncology, Biol. Phys., Vol. 6, pp. 1583 and 1588.

Yerushalmi, et al., published an article entitled "Localized Deep Microwave Hyperthermia in the Treatment of Poor Operative Risk Patients with Benign Prostatic Hyperplasia". This article described initial efforts to heat prostate cancer which involved a substantial amount of the prostate gland. The objective of the treatment described led them to utilize a rectal approach. They used cooling within the rectum to moderate the localized heating of the rectal mucosa, since the EM energy specific absorption rate (SAR) was much higher in this area near the applicator than within the central prostate area.

It should be pointed out that the urethra is usually about 2 cm from the rectal wall. In Benign Prostatic Hypertrophy (BPH) the urethral obstruction is the primary problem for the patient. It would appear unnecessary to treat only the posterior portion of the prostate with heat to relieve a problem primarily confined to the urethral area in the prostate. The concern by Yerushalmi about possible rectal mucosa damage was valid because he was introducing the heating through the rectum. With the urethral approach, rectal heating is not expected to be high because of the 2 cm distance between the urethra and the rectum. Thus, Yerushalmi's use of cooling was to protect the rectal wall from excessive heat damage from the rectal applicator.

Yerushalmi, et al. described their treatments as causing temperatures of 42 to 43 degrees C. in the prostate mass. These temperatures were measured by monitoring the urethral temperature. This temperature range was obtained after 10 to 15 minutes of heating. Each treatment session lasted for 1 hour and treatments were separated by 72 hours delivered twice per week. The patient's condition improved after 6 to 8 treatments, and they claimed the optimal total number of treatments was 12 to 15. Very low toxicity was reported in these cases. However, the article points out that "heating of normal tissue in the applicator-prostate mass path is unavoidable, since high power field energies are required in order to reach the prostatic mass."

Scheiblich and Petrowicz published an article in 1982 in the Journal of Microwave Power entitled "Radiofrequency-Induced Hyperthermia in the Prostate". The system described in the article was solely intended for treatment of cancer of the prostate and not BPH. Cancerous tumors of the prostate are usually quite large and involve a substantial portion of the prostate when they are detected. It is well know that treatment of only a portion of the tumor would not be considered sufficient therapy since the tumor would continue to grow from the untreated portions. This would lead to the same undesirable clinical outcome of uncontrolled tumor growth. Thus, it is important that a cancerous tissue treatment be of the whole volume involved in the malignant growth.

The Scheiblich et al. system described used a rectal approach which included rectal cooling with 2.5 degrees C. cooling water contacting the rectal wall to reduce the local rectal heating. They claimed that they first experimented with a small antenna that was inserted into the urethra but not enough power could be delivered into the prostate through the antenna in the urethra. The details of this design were not described so it is not possible to completely evaluate their claims. The article teaches heating from the remote rectal opening. This allowed a larger diameter antenna and longer diameter water bolus to be used producing a larger heating zone.

Helical coil designs have been used to heat tissues placed within the cylindrical opening of the coil. Such devices are disclosed in U.S. Pat. No. 4,527,550 issued July 1985 to Ruggera. This heating device was not inserted into the body. Another known apparatus is a body passage insertable applicator apparatus for EMR systems which includes a urethral inserted probe having a monopole antenna (Microwave Surgical Treatment of Diseases of Prostate, Harada et el., Urology, December 1985, Vol. XXVI, No. 6, pp. 572-576).

Also known is a helical wound coil applicator having coaxial inner and outer conductors electrically connected at an EMR input end to a conventional coaxial transmission line for transmitting high frequency EMR from a source to the applicator. The applicator coil is attached at one end of the outer conductor segment of the coaxial cable. The inner conductor is electrically connected to the other end of the applicator coil. A dielectric media is disposed between the applicator inner and outer conductors, and the outer conductor and termination end are covered by a dielectric sheath. A uniform, external electric tissue heating field is obtained along the entire length of the applicator radiator by exponentially increasing the thickness of the dielectric sheath over the termination end equal to at least half the outer diameter of the applicator. Those persons skilled in the art, desiring further information concerning this device are referred to U.S. Pat. No. 4,658,836 issued Apr. 21, 1987 to Paul F. Turner. This patent also contains a circulating fluid filled membrane separating the microwave applicator from the tissue while inserted in a natural body orifice. When this device is used it becomes difficult to directly and accurately measure the temperature of the heated tissue using a single temperature sensor which is housed inside of the applicator body or attached to the outer applicator membrane wall. This is because the detected temperature is greatly affected by the temperature of the cooling fluid, and further modified with unknown blood flow effects. Therefore, with current technology, accurate temperature control of the heated portions of the prostate gland with an applicator containing both cooling as well as microwave heating would require measurement with a temperature probe inserted into the prostate tissue. The microwave heating transmits its energy into the tissues of the prostate. The cooling using conductive heat transfer is less capable of affecting temperatures in the deeper tissues and primarily affects the temperature along the applicator tissue interface.

The use of inflatable balloon catheters is also well known in the existing art as described by H. H. Snyder in U.S. Pat. No. 2,936,761. However, the balloon in this type of catheter, often called a Foley catheter, is generally used to hold a catheter from coming out of a body cavity, rather than to position a portion of the catheter in a body passage. Another catheter device made for insertion into body passages for the purpose of measuring the temperature along such body passages was disclosed by Bernard Horn in U.S. Pat. No. 4,046,139. This device uses an inflatable balloon to position a small temperature sensor against the tissue comprising the body passage, but not to position the sensor along the passage.

A European Patent application No. 83305653.4 filed Sep. 22, 1983 by Kureha Kagaku Kogyo described a dipole coaxial applicator embedded in an insertable tube which has a thin polymer layer surrounding the heating zone of the microwave applicator which is inflated with circulating cooling fluid. The described use of the applicator is for the heating of endotract lesions. The prefix endo refers to "inside", which implies use inside of body passages. The metal wire temperature sensor placed on the surface of the fluid circulating membrane would certainly not be able to perform a direct or reliable measurement of the surrounding heated tissue, since the sensor is attached to the coolest point adjacent the applicator, the cooling fluid membrane. It is also known that the linear dipole antenna which he describes doesn't provide uniform heating along length of the antenna, thus the heating would not be very uniform along the body passage. The metal wire sensors have also been shown to modify the heating patterns around the metal wire. This is especially true when the wire is aligned with the microwave radiated electric field as shown in the preferred embodiment of that patent application. It is quite important to assure that prostate treatments are reliable and consistent to provide both safety and effective treatments. To achieve this therapeutic goal, it is important to avoid excessive heating of tissues which might result in patient pain and complications, but, at the same time, adequate temperatures must be obtained for a significant time in the targeted treatment tissues on the prostate gland. A lack of a reliable method to measure the heated prostate tissue temperature surrounding the urethra will result in inconsistent treatment results.

The international patent by Bicher WO 81/03616 describes a microwave antenna for intracavitary insertion. This apparatus contains an inflatable jacket which is filled with air and provided with air circulation tubes to provide some cooling. The air flow would have an effect of cooling the adjacent tissues, but would also result in incorrect temperature measurements of the actual surrounding tissue temperatures from the temperature sensors which are placed along the outer wall of the applicator apparatus.

Recently Diederich and Hynynen described use of a rectally inserted ultrasound array device for the treatment of prostate cancer ("Induction of Hyperthermia Using an Intracavitary Multielement Ultrasonic Applicator", IEEE Trans. on BME, Vol. 36, No. 4, April 1989, pp. 432–438). This article describes several ultrasound cylindrical sleeves along an inserted applicator body. This array construction is relatively large in diameter, so it is suitable for insertion into the rectum, but the construction requirements and application of insertion into the urethra for more local heating of the benign prostate diseases for the purpose of urinary function improvement is not taught.

The use of microwave radiometry as a means of temperature measurement with an inserted heating applicator has been described by Convert. Convert in U.S. Pat. No. 4,312,364 has described the use of an invasive microwave or electromagnetic wave heating probe which is also used to receive with a radiometric receiver, a measure of the thermal noise of the surrounding tissue and deduce therefrom the temperature of these tissues. Convert further suggests using the deduced temperature measurement to control the power emitted through a servocontrol system. The microwave antenna is represented by Convert as being inserted into the tissues of the body using a sharpened tip, hollow slotted needle. This is used to pierce the skin and penetrate into the body tissues by cutting into these tissues. After the antenna is inserted, the insertion needle can then be removed. This is called interstitial therapy where the devices are inserted by cutting into the body. This type of antenna is usually quite small in diameter to avoid the requirement of cutting a large insertion hole into the patient's body. Convert also suggests that a different type of probe may be designed for introduction into the human body by a natural route such as the esophagus. For this purpose, he suggests use of an ovoid dielectric sleeve around the antenna with permittivity similar to the coaxial dielectric, such as silicone. There is no tissue cooling means suggested or possible with the apparatus of Convert, and there is no positioning method provided for properly locating such a device at the correct treatment location. The configuration shown for insertion into the natural body passages has a solid dielectric sleeve, such as a silicone material, which would not cool the passage surface, and, as shown, would not be suitable for insertion or positioning within the prostatic urethra passage.

Other radiometric temperature measurement apparatus have been reported, but none are as closely related as the work reported by Convert, who uses them with an invasive heating device.

SUMMARY OF THE INVENTION

According to the invention, an energy radiation applicator apparatus for treatment of benign prostatic hyperplasia and other diseases of the prostate gland locally involved around the urethra, includes a catheter means for insertion into the urethra, an energy applicator mounted on the catheter, and a connector means extending along the catheter from the energy applicator to outside the body when the catheter is inserted in the urethra. The connector means is adapted to be connected to a source of energy to be supplied to the applicator to enable the applicator to radiate energy to the tissue surround the applicator to elevate the temperature of such tissue to a preselected temperature and to maintain the preselected temperature during treatment.

In a preferred embodiment of the invention, the apparatus includes a fluid receiving means surrounding the applicator so as to be positioned between the applicator and the tissue to be heated, and means for circulating cooling fluid through the fluid receiving means during heating of the tissue to thereby cool the tissue immediately adjacent the applicator. A means for measuring heated tissue temperature is included so that the temperature of the tissue can be maintained within a preset range during treatment, and when cooling is used, preferable takes the form of a radiometer selectively connected through the connector means to the applicator. When so connected, the applicator acts as an antenna to receive energy (thermal noise) transmitted from the heated tissue which is representative of the temperature of the heated tissue and to send such received energy to the radiometer for measurement. This detected temperature information can be used to control the amount of energy applied to the applicator to regulate the tissue temperature. When using a radiometer, the applicator is alternately switched between connection with the energy source and the radiometer.

The energy applicator may be an electromagnetic (EM) energy applicator in which case the applicator can take many known forms, such as a coiled conductor in the catheter, or may be an ultrasonic energy applicator in which case the applicator may take the form of a stack of piezo-electric cylinders in the catheter. The piezo-electric cylinders convert the EM energy into high frequency mechanical movement of the material. This high frequency mechanical movement causes ultrasound radiation to be sent into the tissues surrounding the applicator to cause heating of the tissue.

The catheter preferably includes an applicator positioning means for positioning the applicator in the prostate gland adjacent the tissue to be heated and for maintaining the position during treatment. The applicator is suitably sheathed to provide an external substantially uniform tissue heating field to be radiated at nearly all transverse cross sections along the applicator for substantially uniform tissue heating.

A principal feature distinguishing the present invention from the prior art devices is the provision of a urethral insertable EM or US radiation applicator, system, and method principally adapted for benign prostatic hyperplasia (BPH), which provides the generally cylindrical or longitudinally uniform EM or US radiation heating pattern necessary to enable substantially uniform heating of BPH growths or other tissue diseases associated with the urinary track, by the combined use of circulating cooling fluid inside the applicator and monitoring the heated prostatic tissue temperature by using microwave radiometry. The unique use of microwave or US radiation radiometry with cooling in a microwave or US radiation applicator for the treatment of the prostate has a specific therapeutic advantage not obtained by other methods and systems. This method is capable of greatly improving the therapeutic effect from even one treatment. The hyperthermia treatments with other systems which use an applicator inserted into the urethra do not contain fluid circulation cooling and microwave or US radiation radiometric temperature measurements. The unique combination of these methods enable therapeutic heating of a much larger prostate tissue volume than other methods as well as a reliable and accurate measurement of the therapeutic temperature of the heated prostate tissues. It has been observed in treatments not using cooling in the urethra inserted applicators, that the therapeutic temperatures are limited to about a 6 mm radial depth from the inserted applicator wall. As previously indicated, the tissue layer causing patient problems is usually less than 10 mm in depth, however, in many cases it will be greater than 6 mm, therefore, the therapeutic temperatures may not extend completely through the tissue layer to be heated. In addition, there appears to be the need for between five and ten one hour treatments at temperatures ranging between 43° to 50° C. These treatments are delivered once or twice a week. Early results indicate that there is a greater therapeutic benefit by the delivery of ten treatments as compared to five. The present methods, which are without prostate urethra cooling and microwave radiometry for temperature measurement, cause the greatest tissue temperatures along the applicator/tissue interface. This is because the microwave power is more intense nearest the applicator radiator. This mechanism enables a temperature sensor to be attached to the applicator wall to at least measure the prostate tissue temperatures along the wall. When the cooling is added along the applicator wall, the excessive tissue temperatures are reduced. This enables more power to be introduced to heat a greater volume of tissue to therapeutic levels. Because a larger volume of tissue is heated to a therapeutic level in each treatment, the need for repeated treatments is decreased.

It has been shown in cancer hyperthermia, that when the target tissues have been adequately treated even one or two times, they will completely respond. The response is normally measured by tissue necrosis. These necrotic or dead tissues are normally absorbed and digested by the natural body process of removing dead cells. Thus, adequate treatment of the tissues within the prostate by even one good heat treatment of the entire target mass is expected to result in the full effect of therapy. This could reduce the number of required treatments from about ten to only one or two. This could greatly reduce treatment costs and inconvenience.

The current methods using microwave urethra heating without cooling have been found to treat to a depth of about 0.6 cm and a length of about 4.5 cm. This results in a treated volume of about 9 cm$^3$ for a mass of 9 grams. The most common surgical procedure to correct this urinary blockage or retention and other symptoms of benign prostate diseases is the trans-urethral resection of the prostate (TURP). The TURP procedure normally involves the surgical removal of about 15 to 20 grams of prostate tissue along the urethra passage inside the length of the prostate gland. Thus, less tissue is treated by the heat treatment in the first session, than is surgically removed to resolve the symptoms. After the first treatment with current methods, some of the prostate tissues become necrotic and begin to recede by the body's removal of the dead cells. By the next heat treatment several days later, some of the original tissue is most likely not present. This enables a second heat treatment to adequately heat tissues which were beyond the heating depth of the first treatment. Thus, repeated heating treatments are required to eventually treat sufficient tissues to obtain the therapeutic effect and benefit as is provided by the surgical method of (TURP). By using the circulating fluid cooling within the urethra during microwave treatment, the depth of the therapeutic heating is increased because more power can be radiated without causing excessive temperatures. Excessive temperature would certainly contribute to power limiting pain, and may contribute to undesirable toxicity. The volume of tissue which can therefore be treated to therapeutic temperature levels in the first treatment is about 22 cm$^3$, which is a mass of 22 grams of tissue. This is slightly over that normally resected by a TURP. Thus, the method of cooling within the prostate urethra enables the complete target tissue mass along the prostate urethra to be adequately heated in just one heating session.

To provide for a repeatable and safe therapy, it is important to provide sufficient power to reach these therapeutic levels and maintain these temperatures for typically about 60 minutes. Higher temperatures would enable shorter times, but patient pain may prevent temperatures in excess of about 48° C. It is possible to incorporate temperature sensors in the applicator to attempt to estimate tissue temperature, but this would also require monitoring to the radiated power and require performing occasional tissue cool-down measurements to estimate the effect of blood flow, tissue thermal conduction, and bolus cooling effects. This is not expected to be as reliable in all patients as compared with a direct temperature measurement. The preferred method to measure the prostate tissue temperature is by using the heating applicator in a receive mode to direct the thermal noise in the heated prostate region into a microwave or US radiometer. The temperature measurements of the radiometer provide a measurement which is directly related to the temperature within the prostate tissue volume corresponding to the heating volume. This measurement is comprised of adding the temperature signals from the various tissue cells within the applicator's heating field. Therefore, this measurement is like having thousands of individual temperature points which are measured and then added together to provide an indication of the average temperatures within the heated region. This method does not measure the maximum or the minimum temperature in the heated tissue, but provides an accurate measure of the average tissue temperature within the treatment zone. This new method enables the treatment of benign prostate disease to be efficiently treated with hyperthermia, where the tissue being treated is the same tissue which would have been surgically removed by a TURP.

In many patients there are severe side effects by the TURP procedure such as incontinence, retrograde ejaculation, impotency, and death. It is estimated that between 0.3 to 3% of the patients receiving the TURP surgical procedure die from either the procedure or by other factors related to the procedure. Many patients are poor surgical risks due to their age and poor health. The use of hyperthermia treatments as described herein, represent a non-surgical alternative therapy for the benign prostate disease. The optimal combined utilization of the urethra inserted radiating energy microwave source, the circulation cooling fluid in the urethra, the positioning and urine drainage system of the Foley catheter, and the microwave radiometry provides a very practical method to treat benign prostate disease. It is also feasible that this method will be suitable for the treatment of malignant prostate disease. The malignant prostate disease normally involves a larger size mass requiring treatment than is possible with the urethra inserted applicators. However, the increased treatment volume provided by this new method may enable some malignant prostate tumors to be effectively treated as long as the tumor resides within the therapeutic heating area which extends to about 0.8 cm away from the inserted applicator wall. Certainly if the urethral blockage through the prostate is caused by malignant growth, the use of this method to relieve the blockage symptom is also feasible, even though the intent would possibly not be to cure the cancer if the cancerous growth was larger than the heating volume.

The use of ultrasound crystal cylinders is also considered feasible with this method which can operate as both energy transmitters as well as ultrasound radiometric temperature sensors. In this form, the ultrasonic thermal energy radiated by the tissue within the ultrasound applicator's heating zone will be detected by the ultrasound radiometer. This would therefore be equivalent to the microwave urethral inserted applicator, but would operate at ultrasound frequencies. Various ultrasound cylinders are commonly available such as from The EBL Company of Hartford, Conn. It is preferred that a longitudinal stack of ultrasound crystals be used to enable more flexibility and bending of the inserted crystals.

During radiometry measurements, it is possible that EM noise sources other than the heated tissue, such as fluorescent lights, radio stations, microwave ovens, etc., can interfere with the accurate operation of the EM radiometer. It is possible to perform the application of this EM method inside a metallic shielded room to block out many EM sources which would otherwise possibly interfere with the EM radiometry operation. The addition of a shielded room facility to improve the operation of a radiometer is not considered novel, but is well known in the current application of radiometry. However, where a shielded room is not available, or where other EM sources may be located in the shielded room, it is useful to include an electrically conductive shield or blanket over or around the patient in the treatment area to reduce the effects of these other EM noise sources on the radiometer. Suitable materials for this shielding blanket are metal screen or mesh, such as that produced by Cleveland Wire Cloth Manufacturing Company of Cleveland, Ohio. The conductive sheet may be in the form of a metal impregnated paper such as that produced by Zippertubing Company of Los Angeles, Calif., or by International Paper of Tuxedo, N.Y. The conductive sheet may even be a metal foil sheet which is commonly marketed as aluminum foil. A practical other shielding material is conductive cloth such as that manufactured by Devex S.A. of Denis, Switzerland, or the Hexcel Corporation of Dublin, Calif. It is best that these sheets be connected (or grounded) to the outer conductor of the interconnecting applicator cable 16 shown in the Figures.

Advantages of the present invention is the provision of a low cost, disposable applicator which is an integral part of a modified balloon type Foley catheter for the treatment of BPH. BPH is usually treated by surgery with significant side effects. These side effects include hemorrhage, impotency, anesthetic complications, and technical failures. The use of the combined applicator catheter apparatus involves a treatment which requires no anesthesia or surgery and requires only 1 or 2 hour office visits to accomplish in comparison to post surgical hospitalization. The improvements of using the urethra cooling and the radiometric temperature measurement may enable a single treatment to be adequate to provide sufficient symptomatic relief as compared to the need of many treatments each a few days apart when the cooling is not used.

BRIEF DESCRIPTION OF THE DRAWINGS

Other objects and features of the invention will become more readily apparent from the following detailed description when read in conjunction with the accompanying drawings, in which.

FIGURE I is a view of the urethral insertable EM applicator system showing the schematic diagram in block form.

DETAILED DESCRIPTION OF A PREFERRED EMBODIMENT

Figure 1:
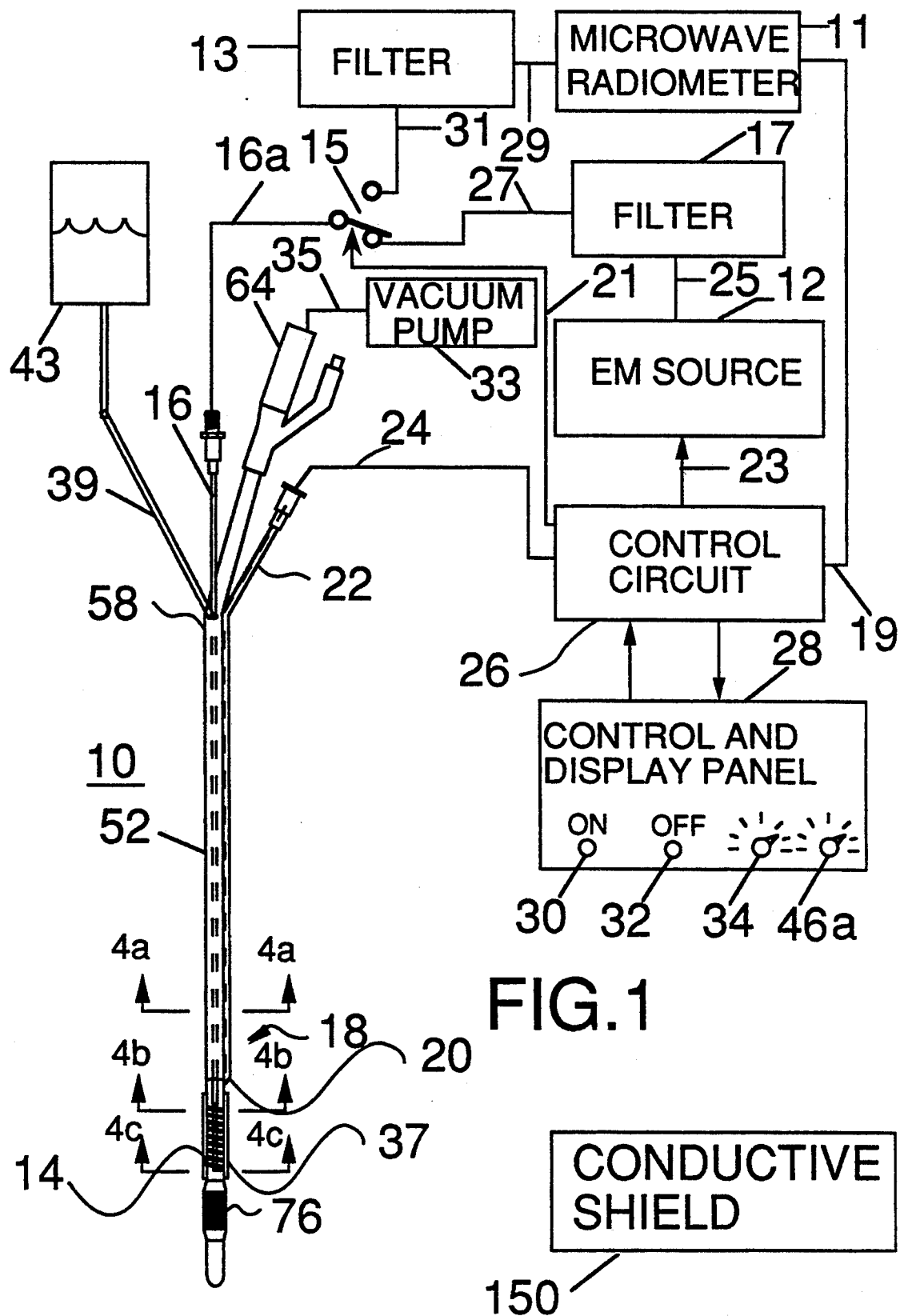

Referring now to FIG. 1, the urethral insertable electromagnetic (EM) radiation applicator system 10 includes an electromagnetic energy source 12 having an oscillator for supplying a maximum 40 watts electrical power at a microwave frequency (typically between 300 to 2450 MHz frequency), for example, to an antenna or applicator 14 through a connector means in the form of a connector cable 16 extending through a catheter 18 from antenna 14 to outside the catheter, and a coaxial cable 16a connected to the end of connector 16. A suitable cable for both the connector cable 16 and coaxial cable 16a is a typical RG-178B cable or one of equivalent size. The antenna 14 is a microwave helical coil mounted in the catheter 18 with the end farthest from the power source 12 preferably soldered to the tip of the solid inner conductor of connector cable 16 and the end closest to the power source preferably soldered to the outer braided conductor of the connector cable 16. The catheter 18 is, for example, a size fourteen French catheter modified as hereinafter described.

The coil of antenna 14 may contain one or more of the following physical features:

a) open connection between the tip of the coil and center coaxial conductor;
b) open connection to the base of the coil and the outer coaxial conductor;
c) conductor breaks or gaps within the coil winding;
d) multiple wrapped coils co-located at the same zone;
e) multiple coils stacked longitudinally and connected to individual coaxial cables to allow modification of the heat pattern length using either coherent or non-coherent phase energy into each coil;
f) flexible straight conductors rather than coiled conductors;
g) a coil with progressively increasing or varying conductor width towards one end of the applicator;
h) a coil with different turns ratio per unit length;
i) diameter variations of the center conductor within the coil length; and
j) modification of the dielectric material or thickness around the center conductor or coil antenna.

Figure 2:
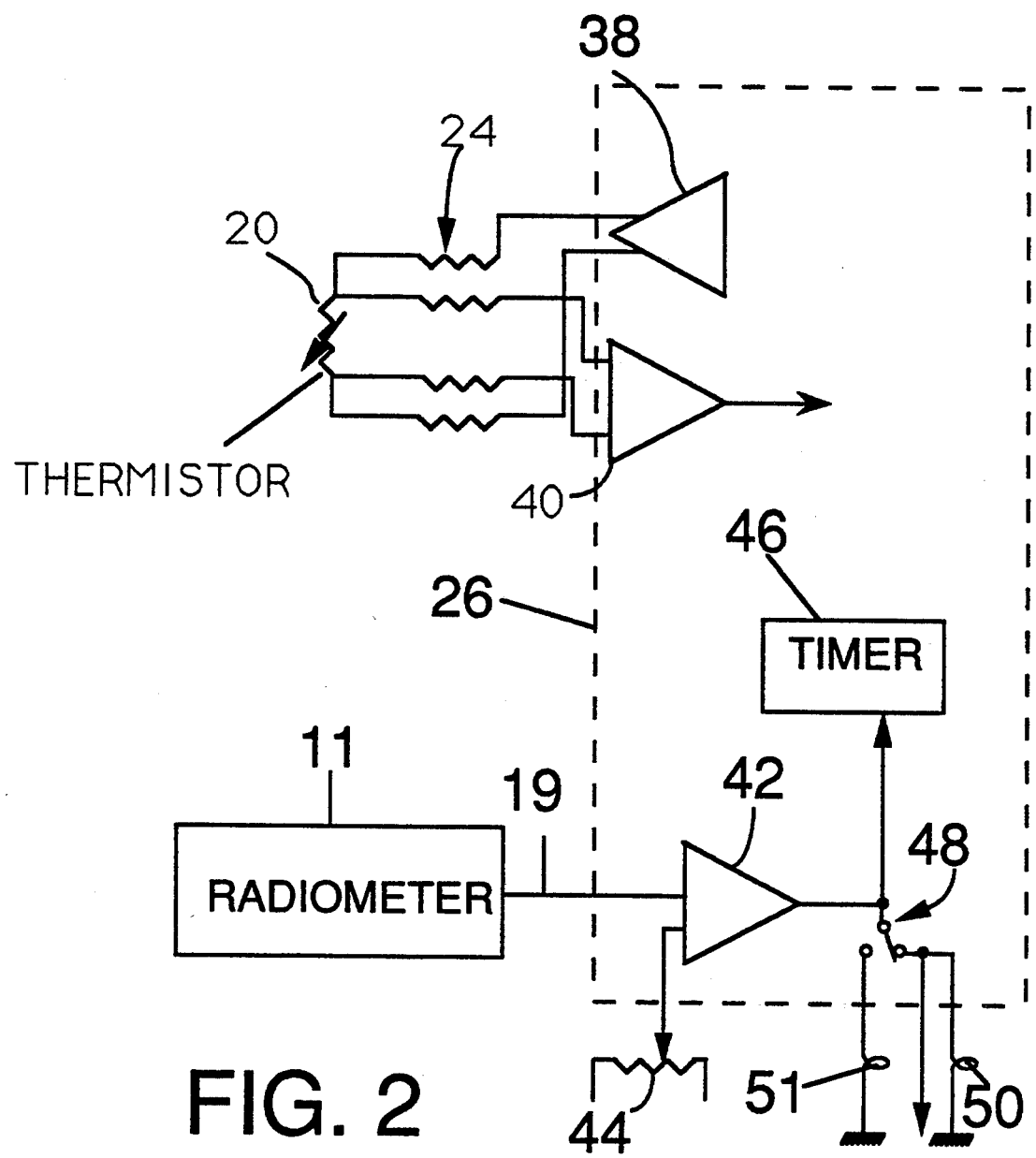
FIG. 2 is a functional schematic view of the temperature sensor and EM source control functional circuits.

A separable insulated temperature sensor 20, FIG. 2, located at the tip of insertable lead 24, is inserted in a flexible tube 22, FIG. 1, during treatment to provide monitoring of tissue temperatures along the length of catheter 18. The insertion depth of the sensor 20 is manually changed within catheter tube 22 to obtain temperature readings along the length of catheter 18.. The tube 22 is attached exteriorly of the catheter 18 and the tip of tube 22 extends almost to antenna 14. The temperature sensor measures the temperature of the urethra tissue surrounding the catheter not located in the prostate. The temperature sensor is connected by an insulated four resistive lead cable 24 to a temperature sensor circuit in control circuit 26 for display and recording functions. The temperature sensor circuit includes a constant current source 38 to provide current to the temperature sensor 20 which is preferably a precalibrated thermistor. An amplifier 40 is connected to the thermistor 20 for amplifying the thermistor output to a working level. While the output of amplifier 40 could be used for control purposes as shown in our parent application, in the illustrated embodiment, the output will usually be connected to a display and used only for information purposes.

A microwave radiometer 11 is connected by cable 29 to an input band pass filter 13 which is connected to a remotely operated function switch 15 with coaxial cable 31. This function switch 15 operates to select either the EM heating mode or the radiometric temperature measurement mode. When switch 15 is in the radiometric mode, the switch connects the microwave radiometer 11 and filter 13 to the applicator coil 14 via the connector cable 16 and coaxial cable 16a. In this mode the thermal energy emitted by the warmed prostate tissue is received by the applicator coil 14 acting as an antenna. This energy is then directed via connector cable 16 and coaxial cable 16a through switch 15 and cable 31, into the filter 13, and through cable 29 to radiometer 11 for detection. The output of radiometer 11 is directed through cable 19 to the control circuit 26 which is used to regulate the tissue temperature by controlling the output power of the EM source 12.

When the switch 15 is in the heating mode of operation, as shown in FIG. 1, the applicator 14 and cables 16 and 16a are connected through cable 27 to the filter 17 and from filter 17, through cable 25, to the EM source 12, whereby the power generated by EM source 12 is directed to applicator 14 and is radiated into the surrounding tissue by the EM applicator 14. The selection of the heating mode or the radiometric temperature measurement mode is controlled by a signal from control circuit 26 through line 21 which is connected between switch 15 and system control circuit 26. Control circuit 26 controls the level of output radiated power from the EM source 12 and is connected to EM source 12 by cable 23. The control circuit 26 has its output connected to the EM source 12 for controlling the EM power source so that it puts out sufficient power to maintain a tissue temperature between about 41.5 degree Celsius to about 47 degree Celsius. A control and display panel 28 is connected to the control circuit 26 for two way communication. The control and display panel 28 includes EM radiation energy on/off switch buttons 30 and 32, and a temperature controller knob 34 for setting the desired operating temperature for the apparatus.

FIG. 1 also shows an elevated sterile water filled chamber or cooling fluid reservoir 43 connected by a tube 39 to a cooling fluid inlet passage 59, FIG. 4, to enable cooling water to flow through a fluid inlet to inflate and flow through a fluid receiving means in the form of a thin walled flexible rubber or plastic cylindrical bolus sleeve 37 which surrounds the radiating applicator 14 to cool the prostate tissues. The fluid filling this bolus 37 is allowed to flow through a small orifice or fluid outlet in the catheter wall into the urine drainage passage. This urine drainage passage acts as a cooling fluid outlet passage and is connected to a drainage connector 64 to enable these fluids to leave the body. To aid in the urine and fluid drainage, the drainage tube connector 64 may be connected to a vacuum pump and storage chamber 33 by a tube 35. In this way, cool fluid stored in the chamber 43 is caused to flow into the bolus 37 inflating the bolus with water, and fluid in the bolus flows out of the body through the connector 64, assisted by the vacuum created by the vacuum pump 33. Vacuum pump 33 preferably includes a fluid storage chamber for receiving and storing the removed waste fluids. It is necessary that the chamber 43 be adequately elevated to inflate the bolus 37. It may be necessary for the chamber 43 to contain a regulated positive pressure pump to assure that adequate inflation of the bolus membrane 37 occurs. This fluid flow provides cooling of the prostate tissues adjacent to the applicator 14 and inserted catheter 18. Also the fluid flow along the input tube 39 flows adjacent to the applicator internal connection cable 16 to provide some regulation of the cable temperature to reduce the effect of the cable temperature on the radiometric thermal detection level.

The microwave radiometer 11 is connected to the control circuit 26, FIG. 1, to direct the radiometric temperature measurement to the control circuit. This enables the control circuit to modify or modulate the EM power output of the EM source 12 to control the tissue temperature to that desired as detected by the microwave radiometer 11. FIG. 2 shows that an amplifier 42 is connected to the radiometer output for amplifying microwave radiometer output signal level. This amplifier function may be incorporated into the radiometer as well. Internal to the microwave radiometer the detected signal must be amplified and integrated (averaged) for about one or two seconds to obtain an accurate measure of the radiometer output. The amplifier 42 also acts as a signal level comparator and has its second input terminal connected to a temperature setting potentiometer 44 which is connected to or controlled by the temperature controller knob 34 located on the control and display panel 28, FIG. 1. Amplifier 42 compares the output of radiometer 11 with a desired temperature reference voltage from potentiometer 44 as set by the temperature control knob 34, FIG. 1, and outputs a temperature difference signal to EM source control signal switch 48. The amplifier 42, FIG. 2, has its output connected to the junction of a timer 46 and an electrically controlled pole of the double pole switch 48. Switch 48 is controlled by the control panel ON switch 30 and OFF switch 32 which enables treatment to proceed. If the ON mode has been selected and the timer 46 had been set by means of knob 46a on control panel 28 to something other than 0 minutes, the output of the comparator 42 will be directed to the EM source 12 by output signal cable 23. If the timer 46 reaches 0 minutes, the output signal of the comparator 42 is prevented from passing to the EM source by being connected to ground in the timer. This prevents microwave output power from the EM source and stops the heating process. The position of switch 48 is shown connecting the output of comparator 42 to the EM source connecting cable 23, which is the position for the ON mode. Also, in this position, current flows through indicator lamp 50 to indicate ON condition. If Timer 46 grounds the signal to stop the heating process, lamp 50 will go out. If the OFF mode is selected by control panel switch 32, the switch position of switch 48 is changed and directs the signal to ground through an indicator lamp 51.

A conductive shield 150 in the form of a sheet or enclosure may be placed over the patient's treatment area or wrapped around the treatment area to reduce the stray electromagnetic noise which may be picked up by the radiometer from other noise sources. These stray signals may degrade the accuracy of the radiometric temperature measurement.

The timer 46, FIG. 2, is triggered by the initial receipt of power from the comparator 42 for measuring a preselected treatment time, and at the end of the timing period cuts off the microwave power source. In addition, the pole of the switch 48 is manually controlled by the ON and OFF switch buttons 30 and 32. When the switch is positioned ON as shown, a control signal is output on lead 23 to power the EM power source; conversely, when the switch 48 is turned to the OFF position, the EM radiation power source is turned off. It should be noted the timer 46. comparator 42, temperature setting potentiometer 44, control switch 48, and other portions of the control circuit can be replaced by a small computer chip such as a microprocessor, operating in an equivalent manner. The use of a small microprocessor performing these represented functions is actually the preferred embodiment of the control system.

Figure 3:
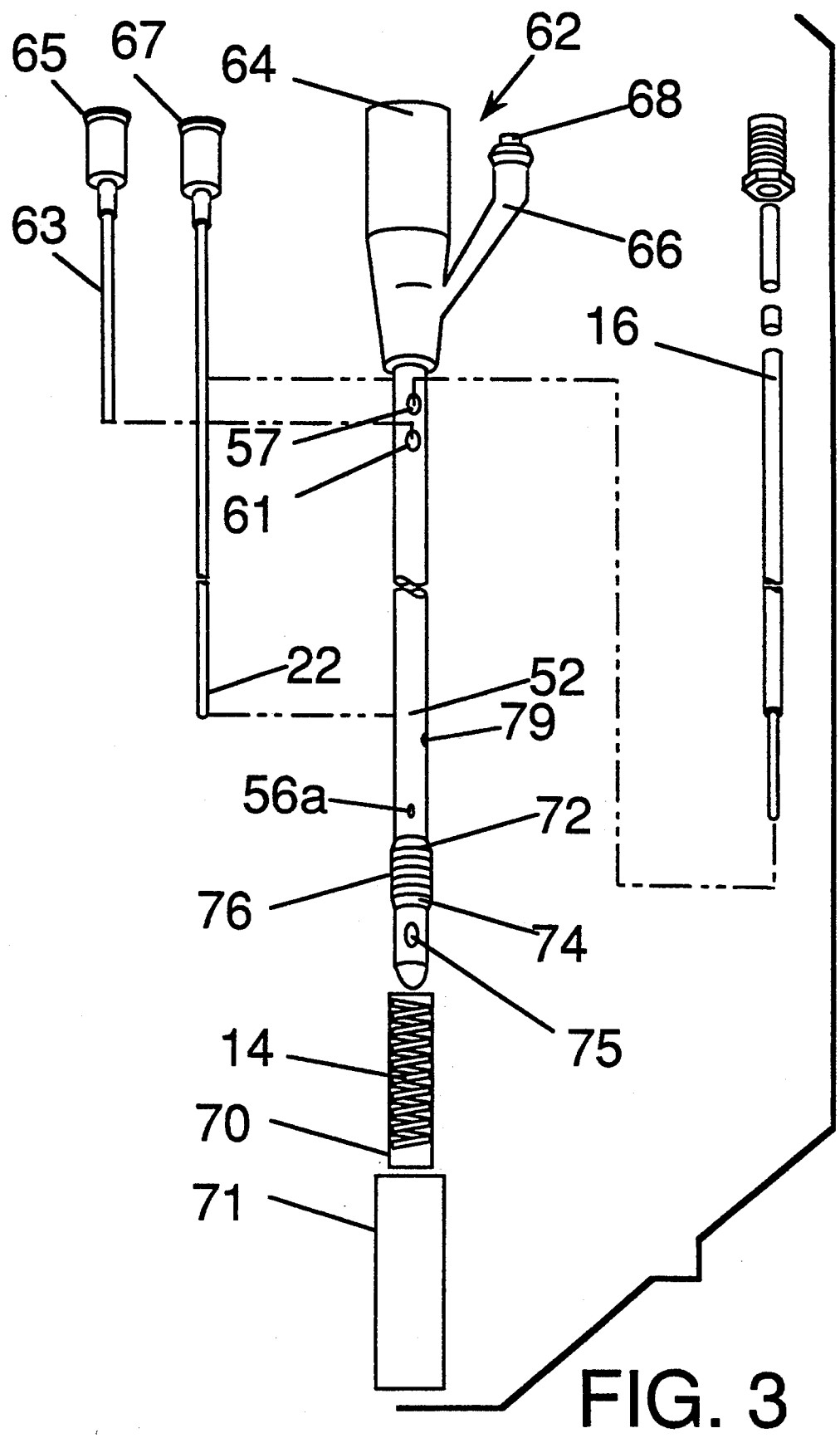
FIG. 3 is an exploded view of the urethral insertable EM applicator.
Figure 4A:
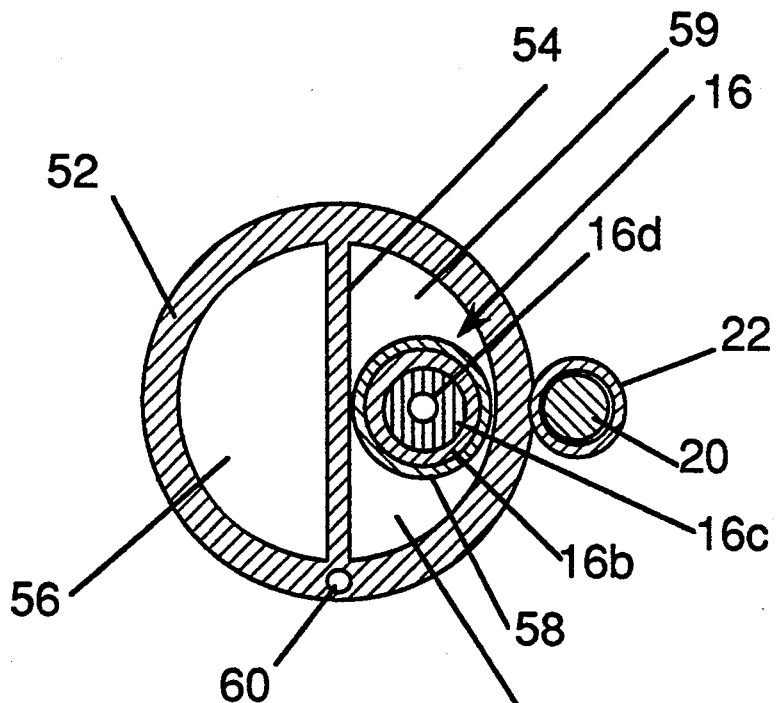
FIG. 4 contains three cross sectional views, FIGS. 4a, 4b, and 4c, of the urethral insertable EM and US applicator assembly; taken on the lines 4a–4a, 4b–4b, and 4c–4c of FIG. 1.
Figure 4B:
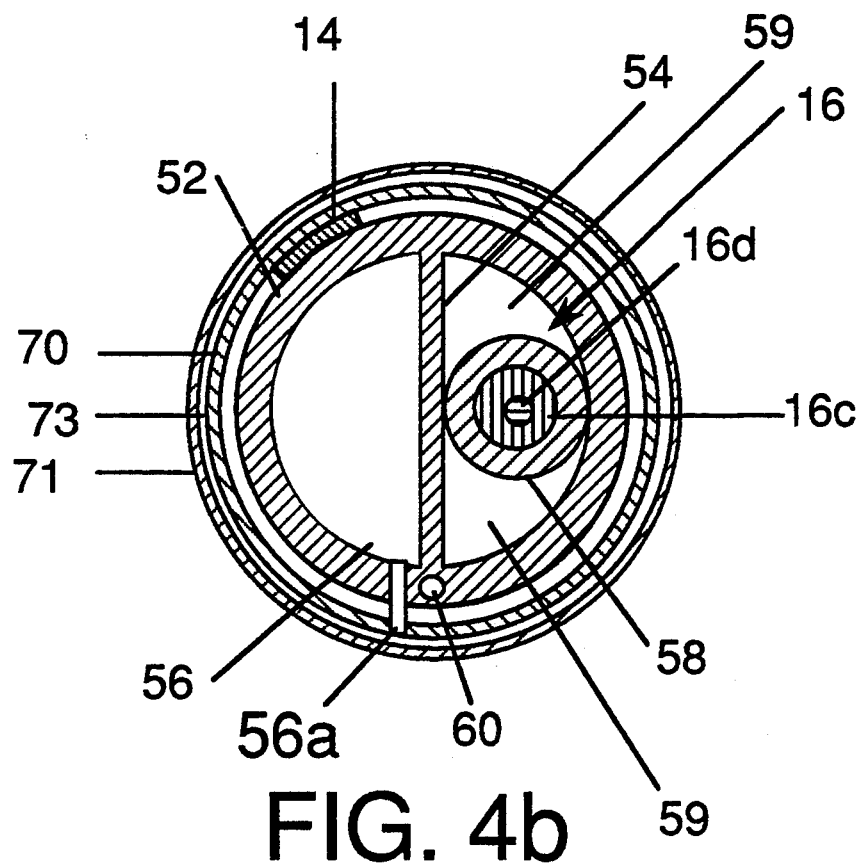
Figure 4C:
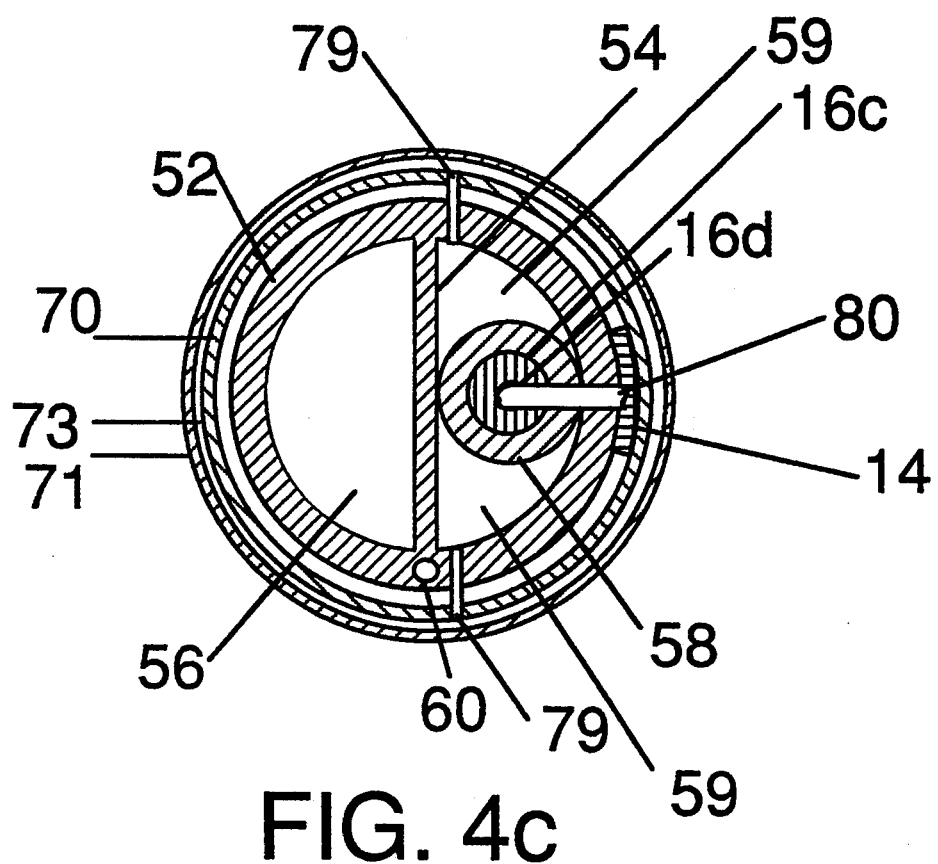

The catheter 18, FIG. 1, of the combined catheter and applicator is, for example, a balloon type urological catheter having a flexible, plastic tubular body 52, FIGS. 3, 4a, 4b, and 4c, which is divided by a partition 54, FIG. 4a4b, and 4c, into a catheter drainage passage 56, a passage 59, and a fluid passage 60 for inflating balloon 76, FIG. 3. The flexible tube 22, FIG. 4a, for the temperature sensor is attached to the exterior of the Foley catheter body 52. The tubular body 52 has a bifurcated opening piece 62, FIG. 3, having one side 64 for connecting the central drainage tube 56 to a waste receiving receptacle or vacuum pump, and a second side 66 having an air or fluid input/output valve 68 for connecting the air or fluid passage 60, FIG. 4a, 4b, and 4c, to a pressurized air or fluid supply source to inflate the balloon 76, FIGS. 1 and 3 after insertion. This air or fluid supply source could simply be a syringe.

Figure 6:
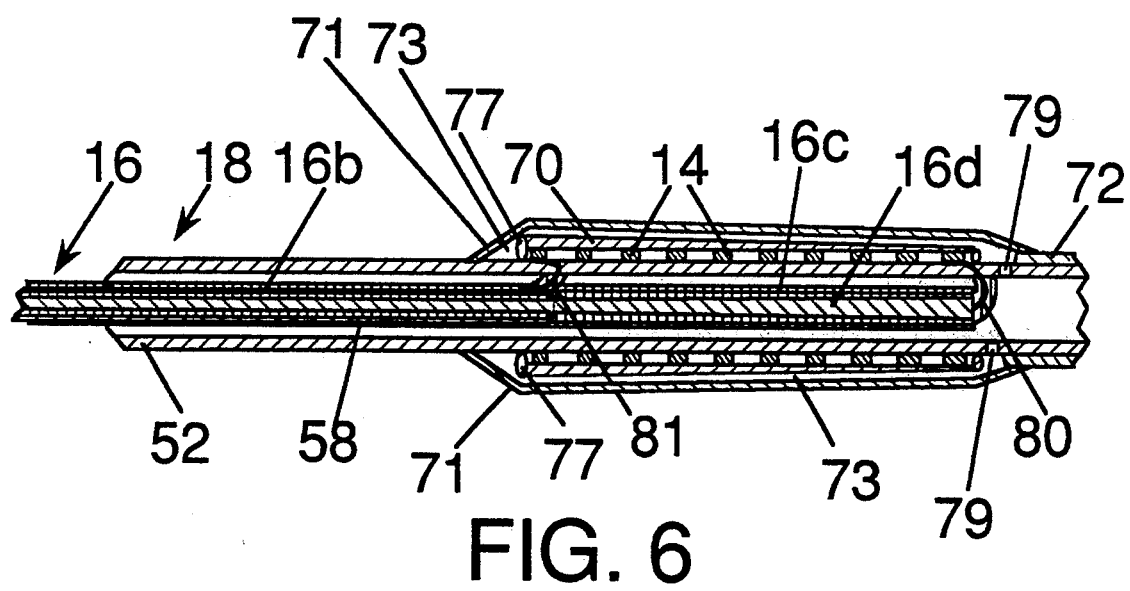
FIG. 6 is a longitudinal section of an EM prostate applicator showing the antenna coil radiating configuration.

The coaxial connector cable 16 with an insulating rubber jacket 58 passes through the hole 57 into catheter passage 59, FIG. 4a. The insulated coaxial cable passes along the inner chamber and connects to the antenna coil 14 as previously described. If cooling fluid is to be circulated through the catheter, catheter passage 59 becomes a cooling fluid inlet passage and will have cooling fluid flowing therein. The coaxial insulating jacket 58 will be sealed in the areas of connection to the antenna 14 to prevent contact with the water or other cooling fluid which will fill this passage 59. The passage 59 is normally connected through hole 61 with an attached tube 63 and connector 65 to the water fluid supply tube 39, FIG. 1. The holes 57 and 61 both lead into the passage 59, so that the coaxial cable 16 rests within and extends along passage 59 in catheter body 18. A pair of openings 79, FIGS. 4c and 6, are provided through catheter wall 52 into passage 59 adjacent to the distal end of applicator 14, which forms a fluid inlet to allow fluid to flow into and partially inflate a fluid receiving area, or chamber, 72, FIG. 4b and 4c, formed by a cylindrical bolus membrane 71. which presses against the tissue walls and separates the membrane 71 from the antenna 14 and its dielectric coating tube 70. This fluid filling the receiving area 71 is allowed to flow through a fluid outlet 56a, FIGS. 4b and 13, into the inner fluid drainage passage 56 which is connected between the tip hole 75 and the drainage connector 64. Fluid drainage passage 56 also serves as a urine drainage tube with tip hole 75 opening into the patients bladder during treatment.

The dielectric coating tube 70 of, for example, silicone rubber, is placed and bonded over the spiral metal coil 14 to complete the applicator. The dielectric coating or sheath 70 is the means for causing the external, electric tissue heating field to be substantially uniform along the length of the applicator. The thickness of the sheath may be varied exponentially if necessary to obtain the uniform heating field. An additional flexible silicone or plastic tube 71 is also placed over the applicator coil 14 and sleeve 70, and bonded at both ends. This enables water to be inserted into the water bolus tube compartment created by the bonded outer sleeve 71. The tip zone inflatable balloon 76 is used to position the applicator body properly within the prostate gland. This balloon 76 is inflated with water or air by the self sealing valve 68, FIG. 3, which is connected by a small connecting tube 60 in the catheter wall 52. The catheter is inserted into the urethra a distance so that balloon 76 is inserted into the bladder prior to being inflated. Balloon 76 in then inflated and pulled back to rest against the bladder neck. The positioning balloon 76 is formed by bonding the cylindrical balloon tubular form at its ends to the catheter body 58 at locations 72 and 74. Thus, the inflatable positioning balloon 76 is positioned between the balloon bonded stops 72 and 74 in open communication with the outlet of the air or fluid passage 60 (FIGS. 4a, 4b, and 4c). Thus, when the catheter is positioned so that the inflated balloon is resting against the neck of the bladder, the applicator is properly positioned with respect to the prostate gland and free from movement for the duration of the hyperthermic treatment.

In operation, with the catheter properly positioned as described above, and the timer 46 of FIG. 2 and the temperature dial set as desired, the EM source 12 of FIG. 1 is turned on by switch 30 and the applicator 14 radiates power into the area of the prostate gland until the desired temperature is reached. When the desired temperature is reached. The comparator 42 outputs control signals to the oscillator to manipulate its EM radiation output power to maintain the radiometric temperature substantially constant for the selected treatment time period. At the end of the treatment time, the EM source is automatically turned off, but the EM source can be turned off at any time using the off switch 32. During the heating period the control circuit actually interrupts the connection of the EM source power through switch 15 to applicator 14 periodically for a few second at a time and connects applicator 14 through mode switch 15 to the radiometer to update the measurement of tissue temperature.

FIGS. 4a, 4b, and 4c show the cross-sectional views taken on the lines 4a–4a, 4b–4b, and 4c–4c respectively, of FIG. 1. FIG. 4a shows the section comprising the major portion of the length of the catheter 18. Passage 60 connects to tip balloon 76. Cooling fluid inlet passage 59 supplies cooling fluid from reservoir 43, FIG. 1, to cooling fluid receiving area 73 shown in FIGS. 4b and 4c. The Coaxial connector cable 16 is routed through the fluid inlet passage 59, and includes a center conductor 16d and an outer conductor 16b, separated by a dielectric 16c. Passage 56 is a fluid drainage passage and also serves as the cooling fluid outlet passage. Passages 59 and 56 are separated by a partition 54. Also shown is the outer attached tube 22 through which the secondary temperature sensor 20 passes to monitor urethra temperature.

FIG. 4b is taken through the zone of the antenna radiating helical coil applicator 14. Between the views 4a and 4b, the outer conductor 16b of connector conductor 16 has been electrically connected to the proximal end of the antenna coil 14 by passing through the catheter wall 52 and the insulating coating 58 of the conductor. This electrical connection must be sealed from the cooling fluids in passage 59 with a dielectric material such as silicone rubber adhesive. Therefore, in FIG. 4b the outer conductor 16b is not seen and the cross-section of the helical conductor strip 14 can be seen. The outer sheath dielectric layer 70 is also seen overlying the conductor 14 and the catheter body 52. Normally the space between the sheath 70 and the catheter body 52 is filled with silicone sealant or adhesive. The flexible outer cylindrical bolus sleeve 71 is also shown forming the outer shell. The fluid receiving chamber 73 between sleeve 71 and sheath 70 is normally filled with a cooling fluid such as water which is supplied by the water storage reservoir 43, FIG. 1, or by some other source of cooling fluid.

FIG. 4c is taken through the zone of the distal connection to the helical coil 14 with the center conductor 16d. This connection is provided by an interconnecting wire 80 and soldering with biocompatible solder. It is not advisable to use lead based solder for such an inserted device, but tin and silver solder is suitable. The fluid outlet opening 56a is used to interconnect the cooling fluid chamber 73 to the fluid drainage passage 56. In this way the circulating cooling water may continue to flow through the fluid chamber 73 which is able to provide substantial tissue cooling through the contacting outer sleeve 71.

Figure 5:
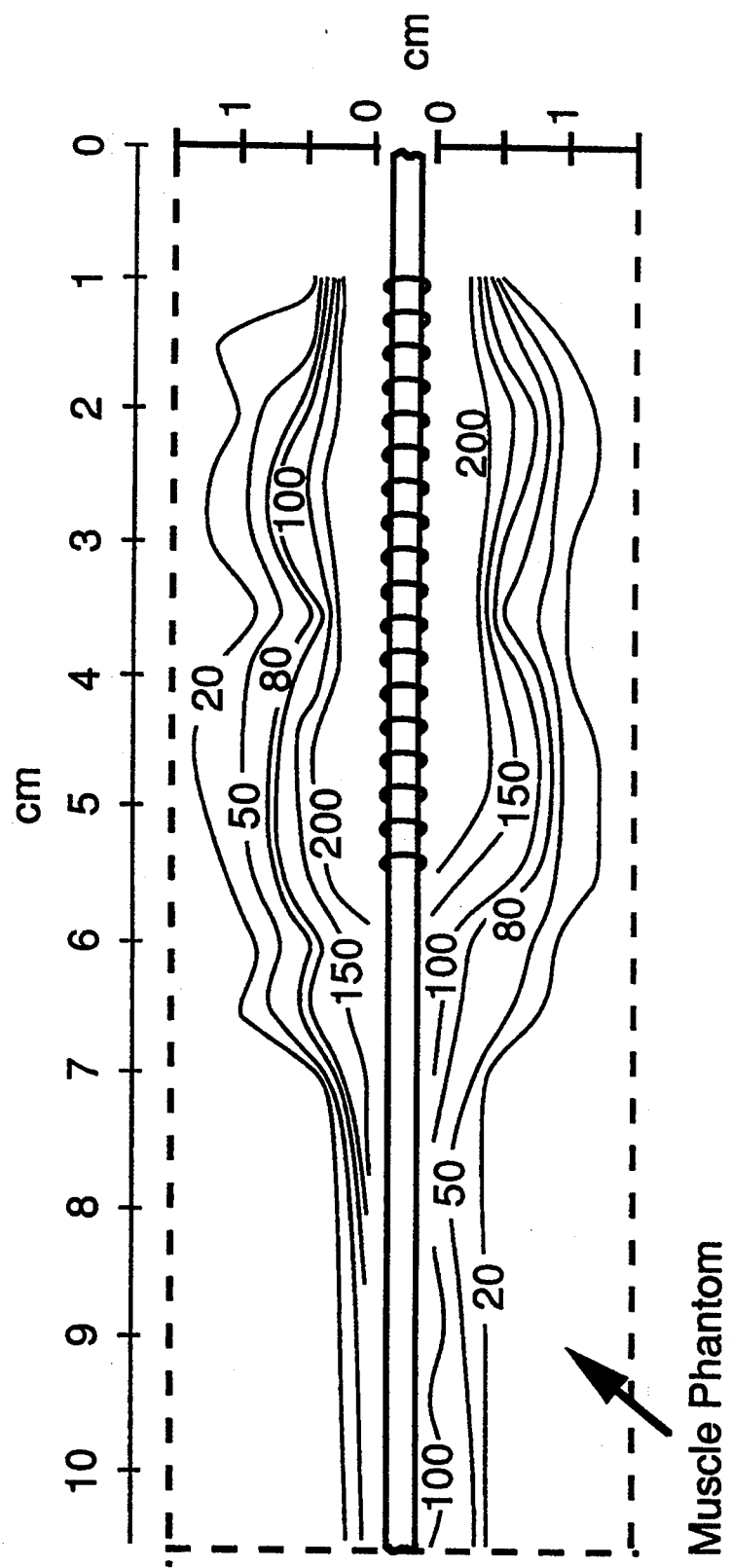
FIG. 5 is a view showing the SAR distribution of the EM prostate applicator measured in prostate tissue equivalent phantom tissue.

The apparatus was tested using muscle equivalent phantom matedal having a relative dielectric=69.0 and conductivity=1.446 mho/m to simulate prostate tissues and the Iso-SAR (specific-absorption-rate) distribution curves charted as shown in FIG. 5. The test parameters were as follows:
Frequency=915 MHz
SAR @100%=115.8 W/Kg
Forward power=20 Watts
Reflected power=2 Watts
Heat-up time=30 Sec.

As shown in FIG. 5, the measurement boundaries were 10 cm. in the x direction and 0 to 1.5 cm to the sides of the applicator body in the y direction. The SAR gradient was 200% down to 20%. The rate of initial temperature rise is proportional with these SAR percentages. Thus, the helical coil type applicator provides a long, uniform, shallow, heat pattern desired for treating diseased tissue found to have spread around and along the body passages.

FIG. 6 shows a cross-sectional view along the long axis of the applicator in the region of the antenna 14. The insulated coaxial cable 16 can be seen passing within the catheter body 52. At the proximal end of the coil 14 the outer conductor 16b is connected to the coil 14 with an insulated wire 81. At this point the outer conductor ends and only the coaxial inner conductor 16d, dielectric sleeve 16c, and insulating sleeve 58 of the coaxial cable extend to the distal region of the coil 14. Also shown is the fluid stop 72 for the tip inflatable balloon 76. The fluid cooling chamber 73 is shown to extend slightly beyond the zone of the coil 14 at both ends. Attachment of the outer flexible bolus membrane 71 is attached at both distal and proximal ends to the catheter body 52 with adhesive such as silicone rubber (not shown). The dielectric sheath 70 may be tapered in thickness, and covers the coil 14 with ends 77 sealed with silicone rubber. The two holes 79 passing through the catheter body 52 to the distal end of fluid chamber 73 enable fluid to pass from the fluid inlet chamber 59 to the bolus fluid receiving chamber 73. These holes in combination with the hole 56a of FIG. 4c enable the fluid to flow from reservoir 43, FIG. 1, through the cooling bolus chamber 73, and be discharged through the drainage connection 64, FIG. 1, into the vacuum pump storage compartment 33. To insure inflation and proper filling of fluid receiving chamber 73, the two inlet holes 79 provide a larger fluid inlet than the single outlet 56a. With this arrangement, it is assured that less fluid can flow from the chamber than can enter it so the chamber will remain full of fluid as long as fluid remains in the fluid supply reservoir.

Figure 7:
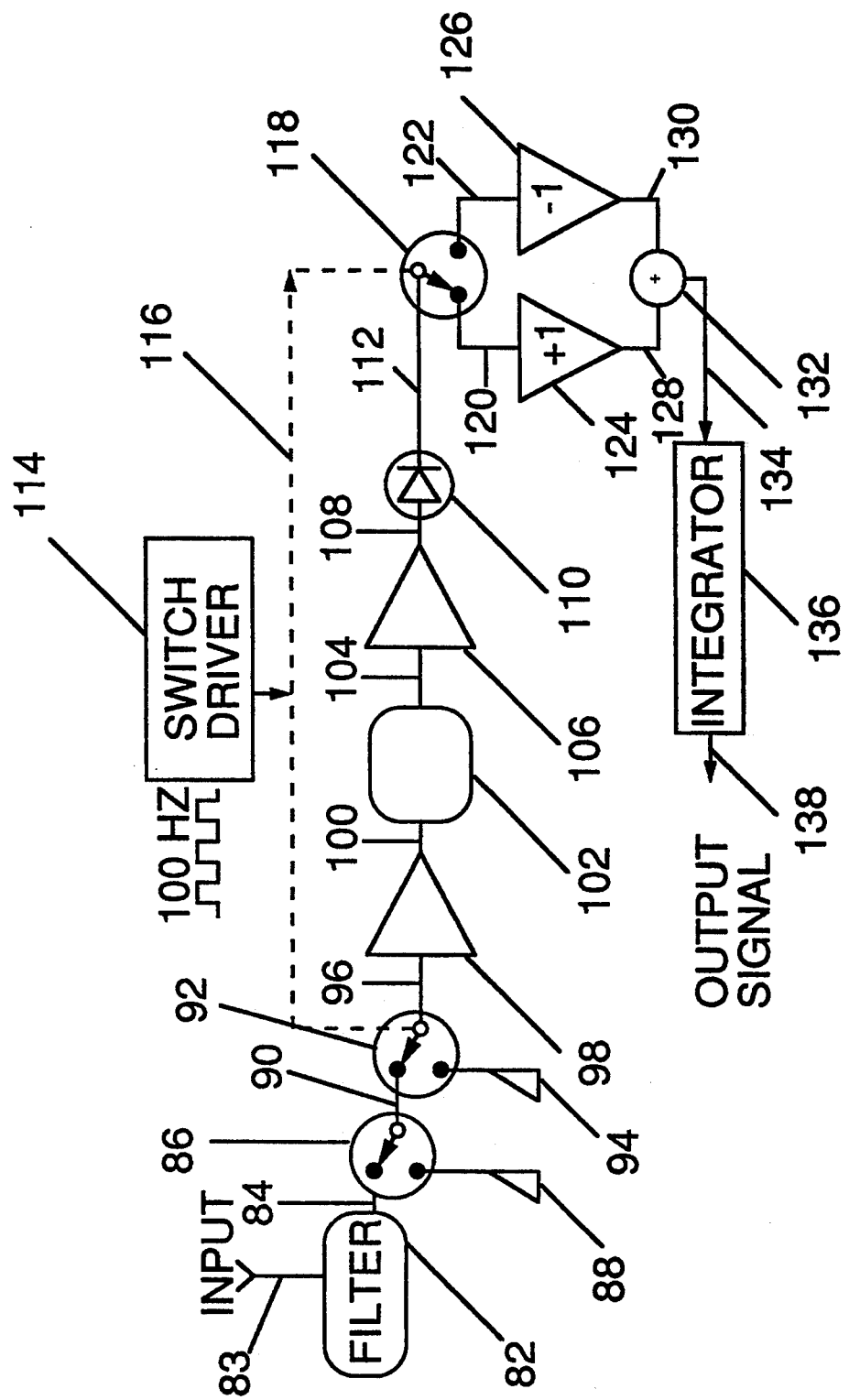
FIG. 7 is a functional block diagram of a Dicke Switch style of radiometer for measurement of tissue radiated thermal noise.

The design of a conventional Dicke Switch radiometer is shown in FIG. 7. The purpose of such a radiometer is to enable very. accurate measurements of very weak energy signals. The input signal as supplied on line 29 from filter 13, FIG. 1, is connected with a transmission line 83 to the input band pass filter 82. This filter is recommended to operate with about a 10 MHz bandwidth at a frequency between 300 to 2450 MHz. The signal is routed to a calibration switch 86 by cable 84 which is normally a mechanical relay coaxial switch. This switch is changed between connection to either the input signal or a constant known temperature resistive load 88. The signal is then routed through cable 90 to a rapidly switched microwave switch called a Dicke Switch 92 which is commonly a solid state switch. The Dicke Switch switches between the signal level and a resistive load 94 at known constant temperature. This Dicke Switch is commonly switched at a rate between 100 to 1000 Hertz driven by the Switch Driver 114 by interconnect cable 116. The switch modulated output of the Dicke Switch 92 is routed to a series of amplifiers 98 and 106 and additional band pass filter 102 with cables 96, 100, and 104. The amplified and filtered signal is then sent by cable 108 to a diode detector and filter 110 to eliminate the microwave portion of the switched signal. The signal is then sent into a demodulating relay switch 118 by cable 112, where the thermal noise signal originating from the resistive load 94 is directed to an inverting unity gain amplifier 126 by cable 122, and the filtered and amplified signal from the input 83 is directed to the non-inverting amplifier of unity gain 124 by cable 120. These two amplifier outputs are added together by a summer 132 and interconnected by cables 128 and 130. The output of the summer 132 represents the dc error voltage signal representing the difference temperature between the input signal and the reference load 94 temperature. This signal is directed to an integrator 136 with a few seconds of integration time by cable 134. The output of the integrator 138 can be interpreted directly as a temperature difference from the reference load 94 physical temperature. Many other types of radiometers are suitable for use with this system as well as the more common Dicke Switch type and should be considered an equivalent part of the described system.

Figure 8:
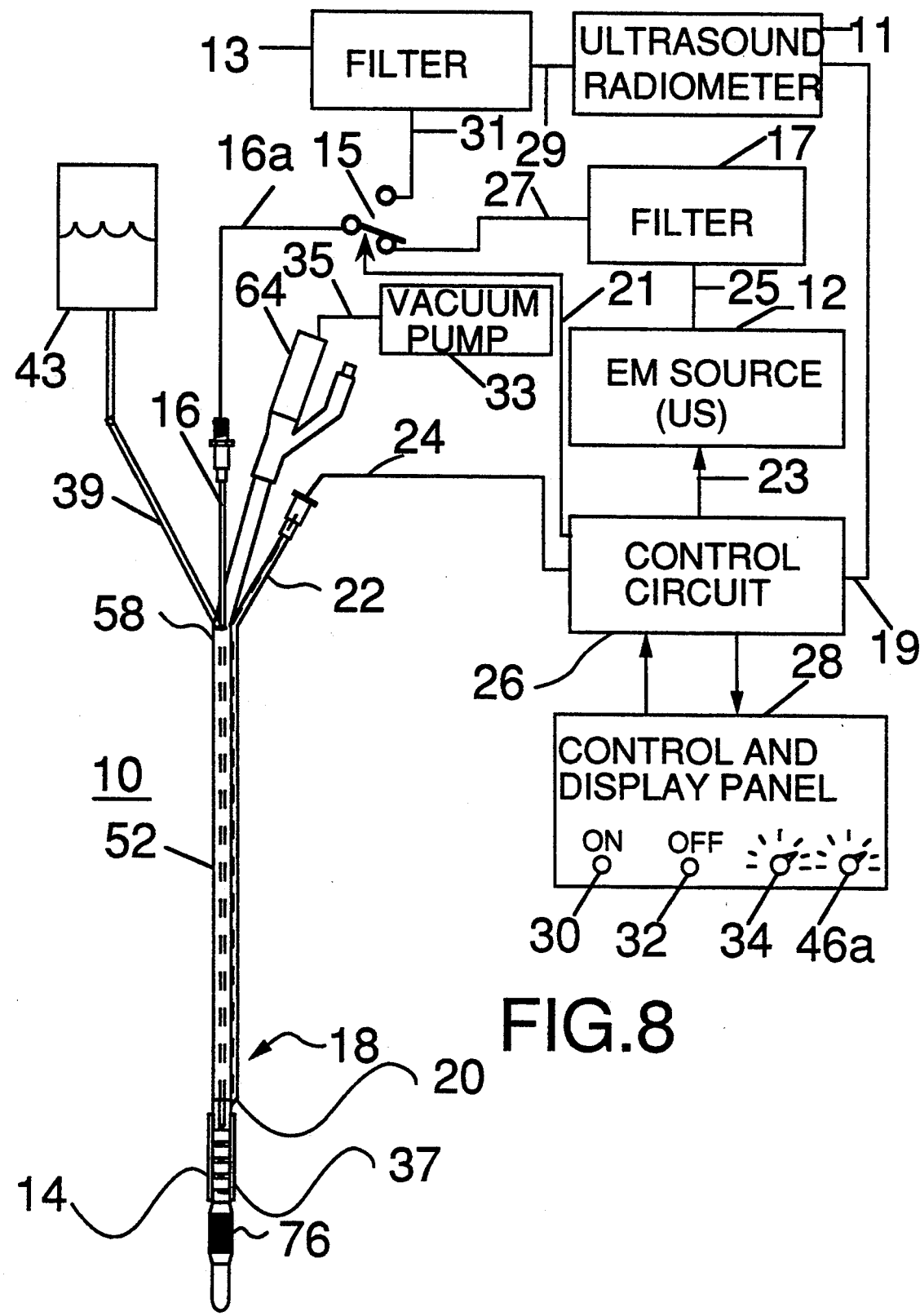
FIG. 8 is a view of the urethral insertable US applicator system showing the schematic diagram in block form.

FIG. 8 is a system diagram similar to that of FIG. 1, but shows the varied components to use an ultrasound radiator 14 and an ultrasound frequency range radiometer 11 which would operate at a frequency of between 0.5 to 5 MHz with a bandwidth of between 10 to 1000 kHz. Note that the EM source 12 would also operate at lower EM frequencies between 0.5 to 5 MHz. All other components operate as previously described.

Figure 9:
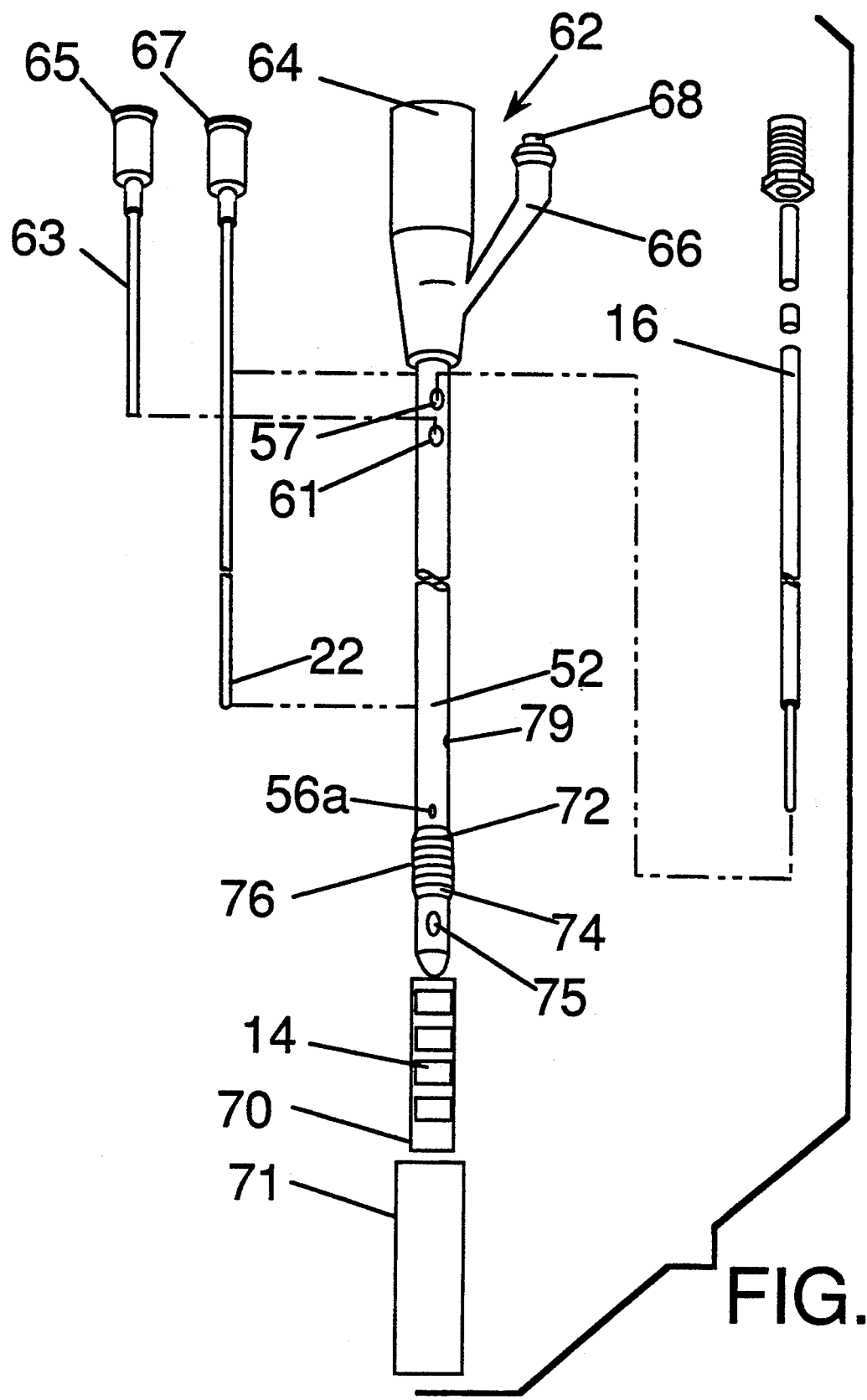
FIG. 9 is an exploded view of the urethral insertable US applicator.

FIG. 9 is similar to FIG. 3, but shows a stack of ultrasound piezo electric cylinders 14 replacing the microwave coil 14 of FIG. 3.

Figure 10:
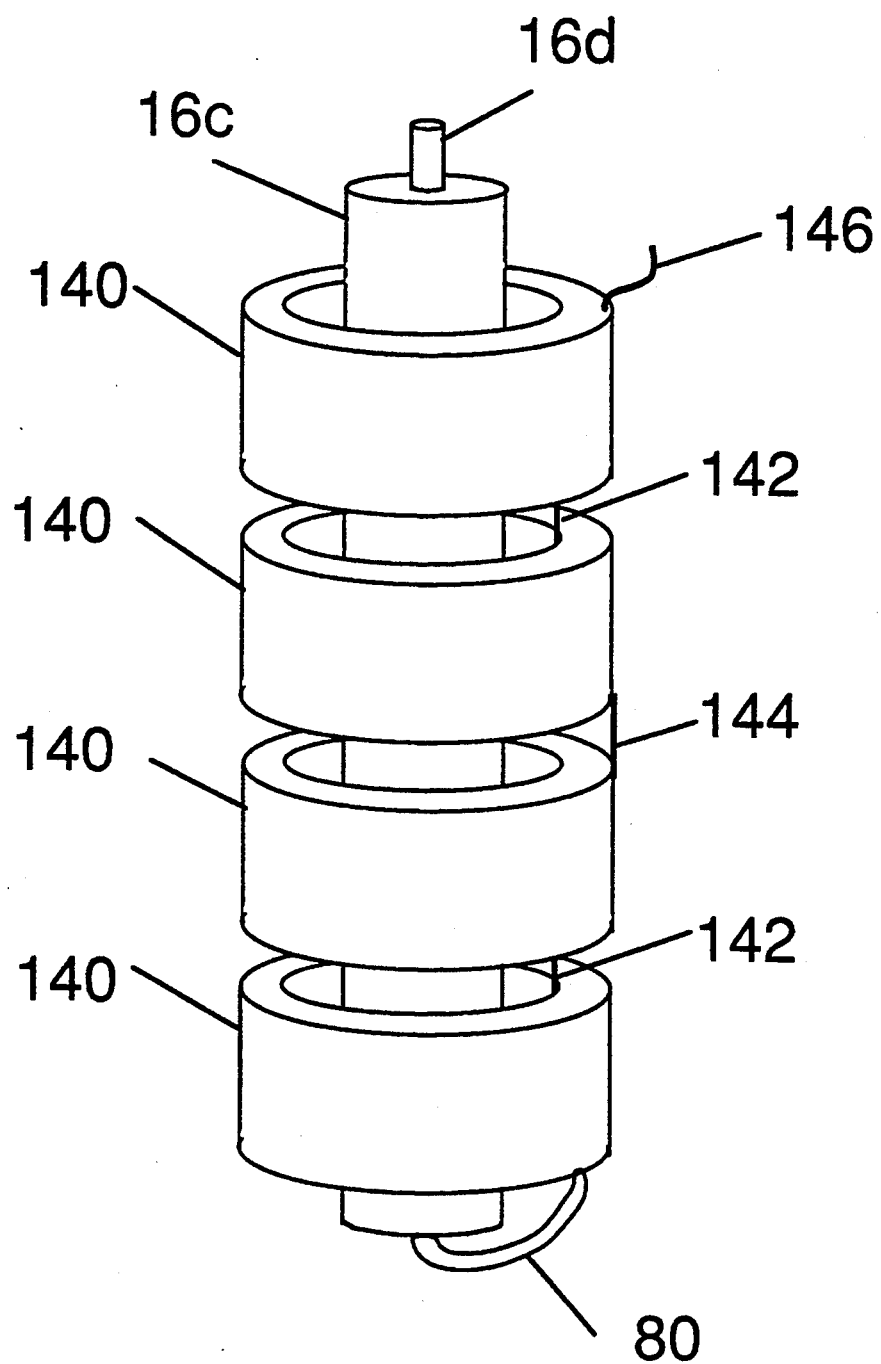
FIG. 10 is a view of the ultrasound radiating transducer cylindrical crystals and their series interconnection.

FIG. 10 shows a more detailed arrangement of the individual piezo electric cylinders 140 comprising the radiating ultrasound stack 14. The coaxial cable 16 is represented where the center conductor 16d passes through the center of the stack and is connected at the distal end of the stack 14 with conductor 80. The cylinders 140 are metal plated on both cylindrical surfaces so the attachment of wire 80 to the outer surface of the most distal cylinder 140 can be made with silver and tin solder. The outer conductor is not shown, but would connect to wire 146. Wires 142 and 144 show series connection of the cylinders 140 to comprise a series connected stack each being soldered as shown. Here the central surfaces of the cylinders are connected together with wires 142 and the outer surface of the cylinders are connected with wire 144.

Figure 11:
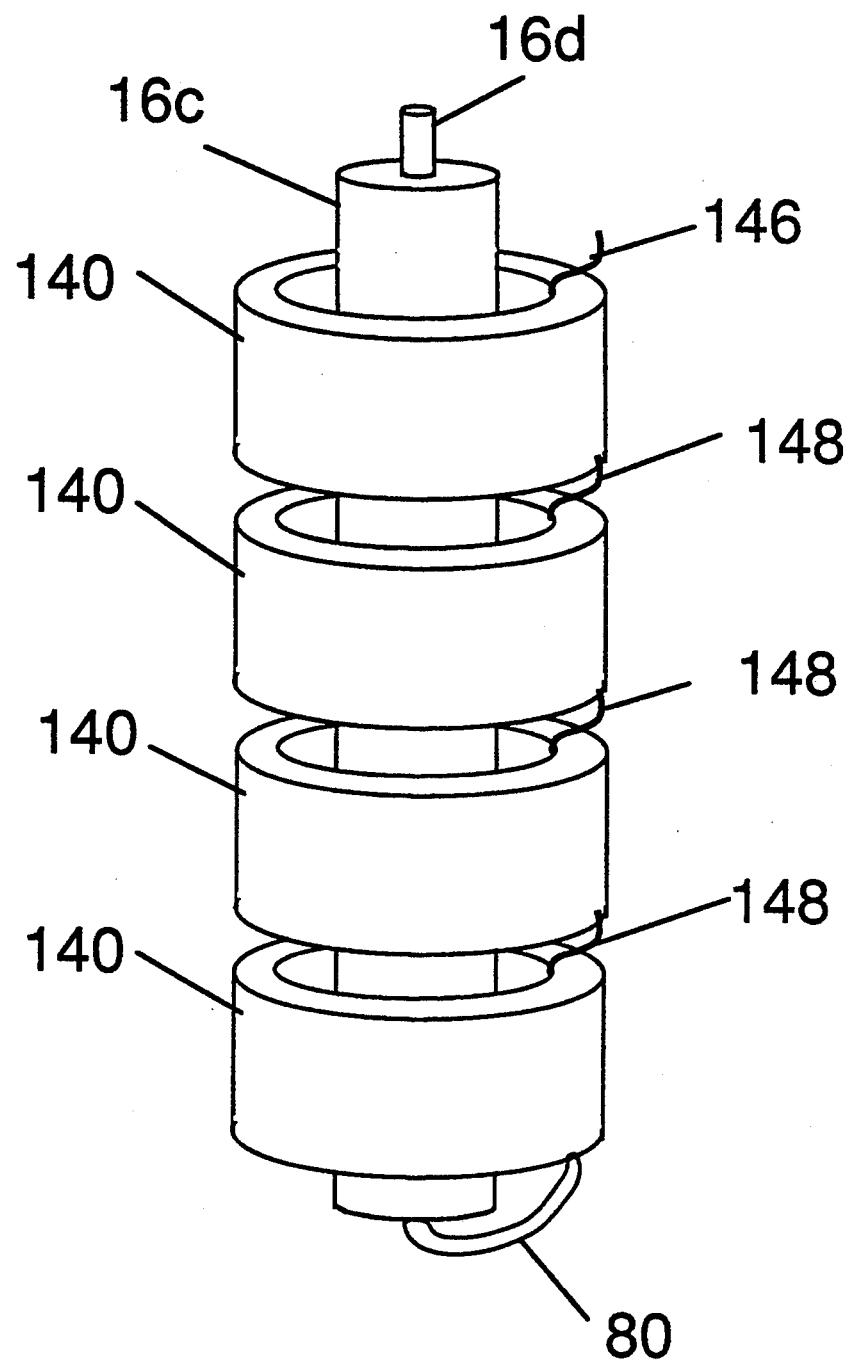
FIG. 11 is a view of an alternate series connection configuration for the ultrasound radiating transducer crystals.

FIG. 11 shows an alternate assembly of the ultrasound piezo electric stack 14 where wires 148 are used to interconnect the cylinders 140 in series. Here the central surface of each cylinder proceeding from the distal end is connected to the outer surface of the adjacent cylinder. The function will be the same for either FIG. 10 or 11.

It is also a part of this invention to measure the temperature of the input and output water flow of the urethral inserted applicator as well as the water flow rate to predict the amount of heating being imparted to the prostate tissue. This could be used either in combination with the microwave or ultrasound radiometry or could be in place thereof. There is a relationship between the amount of power being removed by the urethral cooling and the temperatures reached within the prostate tissues. More importantly there is a relationship between the temperature of the cooling water in the inflated water bolus zone and the temperature of the prostate tissues in contact with the urethral applicator. The limitation of tissue temperatures within the tissues forming the lining of the urethral passage, will provide a limitation to the toxicity and patient complications. It is not certain exactly the preferred limitation of these tissues contacting the urethral applicator, but it is expected that this temperature should be limited to below 45° C. to avoid excessive damage to these urethral tissues. By adding two additional temperature measurement probes to measure both the input water temperature and the output water temperature the temperature of the urethral tissue in contact with the water bolus can be determined as described below.

The heat transferred from the prostate, through the bolus wall, and into the cooling fluid can be quantified using the mass flow equation, q=(dm/dt) Cp (Tout—Tin), where "q" is in the units of kcal/second. The mass flow rate (dm/dt) is determinable and controllable since it is simply a measure of the rate of water flowing through the water bolus, the specific heat of water (Cp) is known to be 1 kcal/kg ° C., and the temperature differential (Tout−Tin) is measurable by locating temperature probes within the applicator body or in the interconnecting tubes. The above enables "q" to be determined from the water flow rate and the measurement of input and output water temperatures. To determine the power "P" which is being removed by the flowing water, the following simple equation is used: P=1.163q. To determine the surface temperature of the urethral prostate tissue in contact with the water bolus zone a simple application of the thermal conduction and convection problem can be used which is the equivalent of Ohm's Law, i.e. [T1−T0]=q r, where "r" is the sum of thermal resistances from the prostate tissue boundary with the applicator, through the bolus wall, and into the cooling fluid. The specific equation is:

$$[T1-T0]=q\{[1/A1(k)]+[1/h(A0)]\},$$

where,
  T1=unknown temperature of tissue
  T0=average temperature of cooling water in the bolus, or, [Tout+Tin]/2
  I=thickness of bolus material
  k=coefficient of thermal conductivity of bolus material (silicone)
  h=coefficient of convection from inside bolus wall into cooling water. Determined by calculating the Reynold's number of flow through the bolus channel.
  A1=surface area on outside surface of the bolus
  A0=surface area on inside surface of the bolus.

So, by controlling and knowing the mass flow rate of the cooling water, and by measuring the temperature rise of the water, the temperature of the prostate surface in contact with the applicator is readily calculated by a system computer or measurable by specialized circuitry to enable the proper amount of power to the tissues to limit the urethra tissue wall temperature to the level below typically 45° C.

In addition, the measure of the forward and reflected microwave or ultrasound power delivered to the applicator as well as the radiating efficiency of the microwave or ultrasound energy radiator can be compared with the amount of power being removed by the water bolus. The power "P" being removed by the bolus can also be used. When adequate clinical information is obtained using prostate tissue measurements with other temperature probes inserted into the prostate, a correlation with the power delivery into the prostate and the power drawn off by the water cooling could be used to directly control the input power for the treatment.

Figure 12:
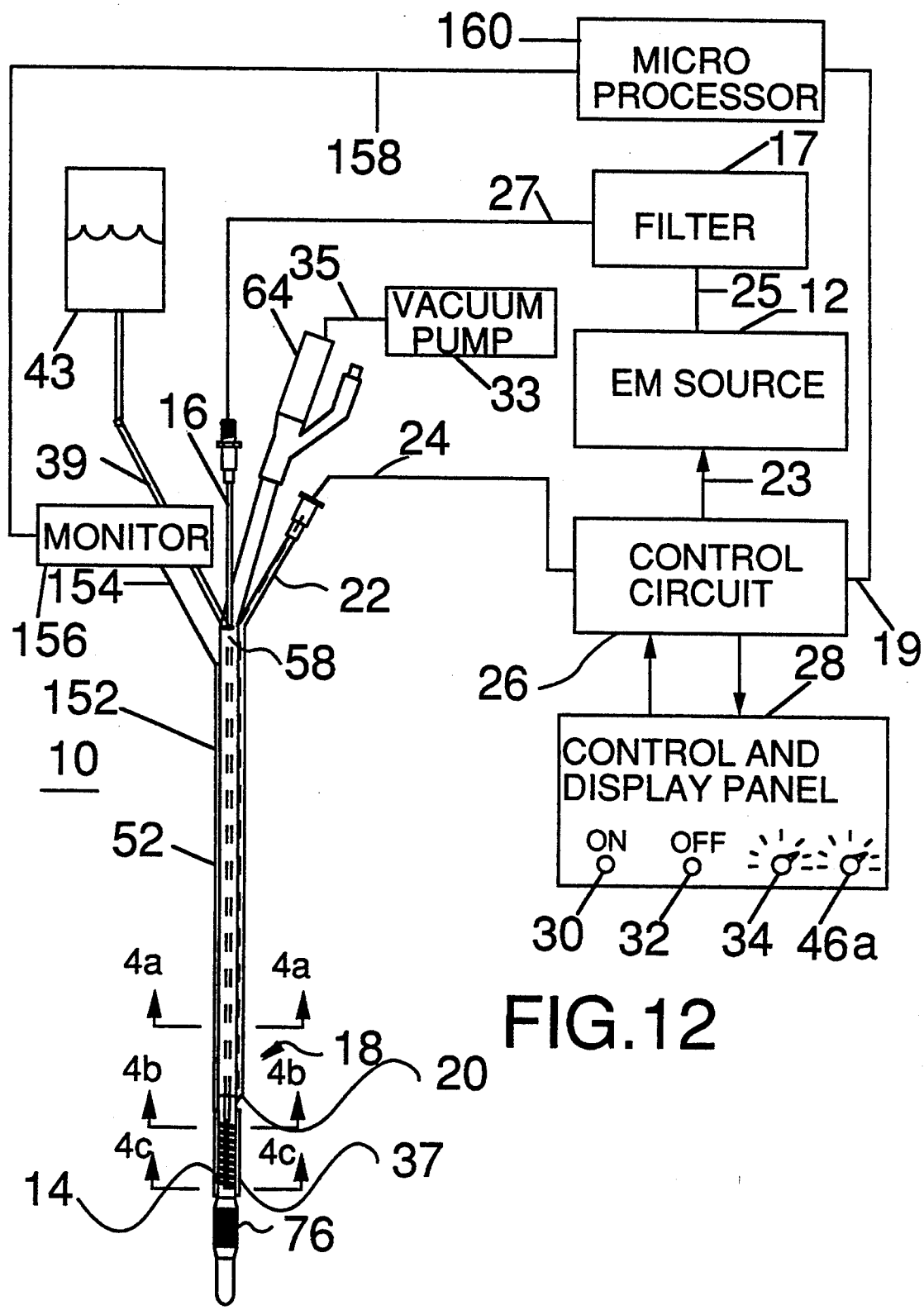
FIG. 12 is a view of an alternate urethral insertable EM applicator system incorporating cooling fluid temperature measurements to determine tissue temperature.
Figure 13:
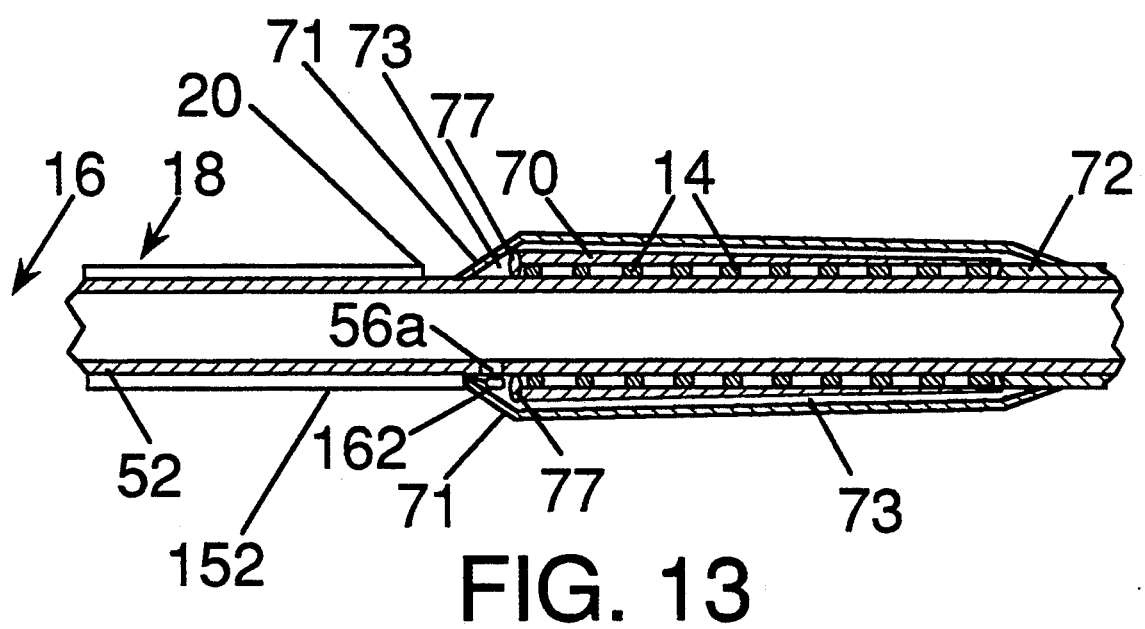
FIG. 13 is a longitudinal section of an EM prostate applicator similar to FIG. 6, but showing the opposite side of the catheter with the fluid drainage passage.

A system incorporating measurement of the inlet and outlet temperatures is shown in FIGS. 12 and 13. A monitor 156 is provided in cooling fluid supply line 39 to measure the temperature and flow of cooling fluid into catheter 18. While the temperature of the outlet fluid could be measured, since it is mixed with urine draining from the bladder which will affect the temperature, it is preferred to measure the temperature of the outlet cooling fluid at the fluid outlet from chamber 73 before the fluid enters outlet passage 56. For this purpose, a temperature sensor 162 is positioned in fluid receiving chamber 73 adjacent fluid outlet 56a as shown in FIG. 13. Resistive leads from temperature sensor 162 extend through a flexible tube 152 secured to catheter 18 similarly to tube 22, and connects to monitor 156. Signals representative of the temperatures and flow of cooling fluid are sent from monitor 156 through cable 158 to microprocessor 160. Microprocessor 160 is programmed to perform the desired calculations as described to provide an output representative of the temperature of the heated tissue. This output from the microprocessor is transmitted through line 19 to the control circuit 26 where it can be used in exactly the same manner as the radiometer signal to control operation of the system as described. In such instances, the microprocessor is substituted for the radiometer in FIG. 2. However, both types of measurement could be used in a system with one or the other or both used for control and/or information purposes.

While the temperature sensor leads for sensor 20 and 162 have been described as resistive, since the sensors only enter the periphery of the energy fields, the resistive leads may not be necessary and normal wire leads could be used.

Whereas this invention is here illustrated and described with specific reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. An energy radiation applicator apparatus for treatment of benign hyperplasia, comprising:
   a catheter means for insertion into and through a urethra of a body needing treatment so an end of the catheter means extends into the bladder of the body, said catheter means including a urine drainage passage extending through the catheter means for draining urine from the bladder;
   applicator means carried by the catheter means, said applicator means including an applicator and a connector means for connecting the applicator to a source of energy sufficient to elevate the temperature of tissue to be treated to a preselected temperature and for maintaining the preselected temperature during treatment;
   fluid receiving means surrounding the applicator so as to be positioned between the applicator and the tissue to be heated;
   a cooling fluid inlet passage extending through the catheter means to communicate with the fluid receiving means through a fluid inlet;
   a cooling fluid outlet passage opening into the urine drainage passage and communicating with the fluid receiving means through a fluid outlet, both the fluid inlet passage and the urine drainage passage opening from the catheter means outside the body when the catheter means is inserted into the urethra;
   means for supplying cooling fluid to the fluid inlet passage during heating of the tissue; and
   positioning means for positioning and maintaining the positioning of the catheter means in the urethra so that the applicator means attached to the catheter means is and remains positioned adjacent to prostate tissue to be treated for as long as desired by the user.

2. An energy radiation applicator apparatus according to claim 1, wherein the cooling fluid outlet passage connects to the urine drainage passage intermediate its length through the catheter means.

3. An energy radiation applicator apparatus according to claim 2, wherein a source of vacuum communicates with the urine drainage passage opening from the catheter means outside a body in which the catheter means is inserted to draw cooling fluid and urine from the urine drainage passage.

4. An energy radiation applicator apparatus according to claim 2, including a cooling fluid reservoir outside the body and in communication with the cooling fluid inlet passage, and wherein the cooling fluid reservoir is positioned to cause flow of fluid into the fluid receiving means to fill the fluid receiving means with cooling fluid.

5. An energy radiation applicator apparatus according to claim 4, additionally including means for measuring the temperature of the cooling fluid entering the inlet passage, and means for measuring the temperature of the cooling fluid leaving the fluid receiving means, the difference in temperature being a function of the temperature of the tissue being heated.

6. An energy radiation applicator apparatus according to claim 5, including means for measuring the flow of cooling fluid through the fluid receiving means.

7. An energy radiation applicator apparatus according to claim 1, additionally including means for measuring a parameter indicative of the temperature of the heated tissue surrounding the applicator.

8. An energy radiation applicator apparatus according to claim 7, wherein the means for measuring a parameter indicative of the temperature of the tissue measures a parameter indicative of the energy applied to the tissue surrounding the applicator.

9. An energy radiation applicator apparatus according to claim 1, wherein the applicator is adapted to radiate ultrasonic energy and includes a plurality of piezoelectric elements.

10. An energy radiation applicator apparatus according to claim 1, wherein the applicator is adapted to radiate electromagnetic energy and includes a helical coil antenna.

11. An energy radiation applicator apparatus for treatment of benign hyperplasia, comprising:
a catheter means for insertion into a urethra of a body needing treatment;
applicator means carried by the catheter means, said applicator means including an applicator and a connector means for connecting the applicator to a source of energy sufficient to elevate the temperature of tissue to be treated to a preselected temperature and for maintaining the preselected temperature during treatment;
fluid receiving means surrounding the applicator so as to be positioned between the applicator and the tissue to be heated;
means for circulating cooling fluid through the fluid receiving means during heating of the tissue;
positioning means for positioning and maintaining the positioning of the catheter means in the urethra so that the applicator means attached to the catheter means is and remains positioned adjacent to prostate tissue to be treated for as long as desired by the user;
means for measuring the temperature of cooling fluid prior to being circulated through the fluid receiving means; and
means for measuring the temperature of the cooling fluid after being circulated through the fluid receiving means, the difference in temperature being a function of the temperature of the tissue being heated.

12. An energy radiation applicator apparatus according to claim 1, wherein the means for circulating cooling fluid through the fluid receiving means includes a fluid inlet through which cooling fluid is supplied to the fluid receiving means and a fluid outlet through which fluid flows from the fluid receiving means, said fluid inlet and fluid outlet being positioned with respect to the fluid receiving means so that fluid flowing from the inlet to the outlet will flow substantially through the fluid receiving means.

13. An energy radiation applicator apparatus according to claim 12, wherein the catheter means includes a cooling fluid inlet passage extending through the catheter means to communicate with the fluid inlet, and a cooling fluid outlet passage extending through the catheter means to communicate with the fluid outlet, both the fluid inlet passage and the outlet passage opening from the catheter means outside the body when the catheter means is inserted into the urethra.

14. An energy radiation applicator apparatus according to claim 13, wherein the fluid outlet is smaller than the fluid inlet [opening] to cause fluid pressure build up in the fluid receiving means to thereby insure the presence of fluid in the fluid receiving means when fluid is provided to the fluid inlet.

15. An energy radiation applicator apparatus according to claim 11, including means for measuring the flow of cooling fluid through the fluid receiving means.

16. An energy radiation applicator apparatus according to claim 11, wherein the applicator is adapted to radiate ultrasonic energy and includes a plurality of piezo-electric elements.

17. An energy radiation applicator apparatus according to claim 11, wherein the applicator is adapted to radiate electromagnetic energy and includes a helical coil antenna.

18. An energy radiation applicator apparatus according to claim 11, wherein the means for circulating cooling fluid through the fluid receiving means includes a cooling fluid reservoir outside the body and in communication with the fluid receiving means, and wherein the cooling fluid reservoir is positioned to allow flow of fluid into the fluid receiving means to fill the fluid receiving means with cooling fluid.

19. An energy radiation applicator apparatus for treatment of benign hyperplasia, comprising:
a catheter means for insertion into a urethra of a body needing treatment;
applicator means carried by the catheter means, said applicator means including an applicator and a connector means extending through the catheter means to outside the body for connecting the applicator to a source of energy sufficient to elevate the temperature of tissue to be treated to a preselected temperature and for maintaining the preselected temperature during treatment;
fluid receiving means surrounding the applicator so as to be positioned between the applicator and the tissue to be heated;
means for circulating cooling fluid through the fluid receiving means during heating of a tissue; and
means for measuring properties of the cooling fluid indicative of the temperature of the tissue being heated to thereby obtain an estimate of the temperature of the tissue being heated.

20. An energy radiation applicator apparatus according to claim 19, additionally including
energy measurements means; and
means for selectively coupling the connector means to either a source of energy sufficient to elevate the temperature of tissue surrounding the applicator to a preselected temperature and for maintaining the preselected temperature during treatment, or to the energy measurement means whereby energy received by the applicator from tissue surrounding the applicator is connected to the energy measurement means and is measured, the energy measured being indicative of the temperature of the tissue being heated and serving as a second measurement of such temperature.

* * * * *

UNITED STATES PATENT AND TRADEMARK OFFICE
CERTIFICATE OF CORRECTION

PATENT NO.   : 5,344,435
DATED        : September 6, 1994
INVENTOR(S)  : Paul F. Turner et al.

It is certified that error appears in the above-identified patent and that said Letters Patent is hereby corrected as shown below:

Column 21,
Lines 35-36, after "according to claim", please delete "1" insert -- 11 --.

Signed and Sealed this

Third Day of December, 2002

JAMES E. ROGAN
*Director of the United States Patent and Trademark Office*